United States Patent
Njikang et al.

(10) Patent No.: US 11,083,684 B2
(45) Date of Patent: Aug. 10, 2021

(54) DERMAL FILLER COMPOSITIONS

(71) Applicant: Allergan, Inc., Irvine, CA (US)

(72) Inventors: Gabriel N. Njikang, Orcutt, CA (US); Xiaojie Yu, Irvine, CA (US); Futian Liu, Sunnyvale, CA (US); Nicholas J. Manesis, Summerland, CA (US)

(73) Assignee: ALLERGAN INDUSTRIE, SAS, Pringy (FR)

( * ) Notice: Subject to any disclaimer, the term of this patent is extended or adjusted under 35 U.S.C. 154(b) by 0 days.

(21) Appl. No.: 14/928,634

(22) Filed: Oct. 30, 2015

(65) Prior Publication Data

US 2016/0113855 A1     Apr. 28, 2016

Related U.S. Application Data

(63) Continuation of application No. 13/706,221, filed on Dec. 5, 2012, and a continuation-in-part of application No. 13/615,193, filed on Sep. 13, 2012, and a continuation-in-part of application No. 13/593,313, filed on Aug. 23, 2012, now Pat. No. 9,393,263, and a continuation-in-part of application No. 13/486,754, filed on Jun. 1, 2012, now Pat. No. 9,149,422.

(60) Provisional application No. 61/568,618, filed on Dec. 8, 2011, provisional application No. 61/534,780, filed on Sep. 14, 2011, provisional application No. 61/527,335, filed on Aug. 25, 2011, provisional application No. 61/493,309, filed on Jun. 3, 2011.

(51) Int. Cl.

| | |
|---|---|
| *A61K 8/73* | (2006.01) |
| *A61L 27/20* | (2006.01) |
| *A61L 27/52* | (2006.01) |
| *A61Q 19/00* | (2006.01) |
| *C08B 37/08* | (2006.01) |
| *A61K 8/04* | (2006.01) |
| *A61Q 19/08* | (2006.01) |

(52) U.S. Cl.
CPC .............. *A61K 8/735* (2013.01); *A61K 8/042* (2013.01); *A61L 27/20* (2013.01); *A61L 27/52* (2013.01); *A61Q 19/00* (2013.01); *A61Q 19/08* (2013.01); *C08B 37/0072* (2013.01); *A61K 2800/91* (2013.01); *A61L 2400/06* (2013.01); *A61L 2430/34* (2013.01)

(58) Field of Classification Search
CPC ......... A61K 8/735; A61Q 19/00; A61Q 19/08
See application file for complete search history.

(56) References Cited

U.S. PATENT DOCUMENTS

| | | |
|---|---|---|
| 2,128,827 A | 8/1938 | Killian |
| 3,548,056 A | 12/1970 | Eigen et al. |
| 3,763,009 A | 10/1973 | Suzuki |
| 3,949,073 A | 4/1976 | Daniels et al. |
| 4,060,081 A | 11/1977 | Yannas et al. |
| 4,140,537 A | 2/1979 | Luck et al. |
| 4,233,360 A | 11/1980 | Luck et al. |
| 4,273,705 A | 6/1981 | Kato |
| 4,279,812 A | 7/1981 | Cioca |
| 4,424,208 A | 1/1984 | Wallace et al. |
| 4,501,306 A | 2/1985 | Chu et al. |
| 4,582,640 A | 4/1986 | Smestad et al. |
| 4,582,865 A | 4/1986 | Balazs et al. |
| 4,605,691 A | 4/1986 | Balazs et al. |
| 4,636,524 A | 1/1987 | Balazs |
| 4,642,117 A | 2/1987 | Nguyen et al. |
| 4,657,553 A | 4/1987 | Taylor |
| 4,713,448 A | 12/1987 | Balazs |
| 4,716,154 A | 12/1987 | Malson et al. |
| 4,772,419 A | 9/1988 | Malson et al. |
| 4,803,075 A | 2/1989 | Wallace et al. |
| 4,886,787 A | 12/1989 | De Belder et al. |
| 4,896,787 A | 1/1990 | Delamour et al. |
| 5,009,013 A | 4/1991 | Wiklund |
| 5,017,229 A | 5/1991 | Burns et al. |
| 5,087,446 A | 2/1992 | Suzki et al. |
| 5,091,171 A | 2/1992 | Yu et al. |
| 5,137,723 A | 8/1992 | Yamamoto et al. |
| 5,143,724 A | 9/1992 | Leshchiner et al. |
| 5,246,698 A | 9/1993 | Leshchiner et al. |
| 5,314,874 A | 5/1994 | Miyata et al. |
| 5,328,955 A | 7/1994 | Rhee et al. |
| 5,356,883 A | 10/1994 | Kuo et al. |
| 5,399,351 A | 3/1995 | Leshchiner et al. |

(Continued)

FOREIGN PATENT DOCUMENTS

| | | |
|---|---|---|
| CA | 949965 | 6/1974 |
| CA | 2805008 | 1/2012 |

(Continued)

OTHER PUBLICATIONS

Prasetyo, A. D. et al., Clinical, Cosmetic and Investigational Dermatology, "Hyaluronic acid fillers with cohesive polydensified matrix for soft-tissue augmentation and rejuvenation: a literature review", 2016, vol. 9, pp. 257-280 (Year: 2016).*

(Continued)

*Primary Examiner* — Bahar Craigo
(74) *Attorney, Agent, or Firm* — Nathan S. Smith; Morgan, Lewis & Bockius LLP

(57) ABSTRACT

The present invention provides highly injectable, long-lasting hyaluronic acid-based hydrogel dermal filler compositions made with a di-amine or multiamine crosslinker in the presence of a carbodiimide coupling agent.

26 Claims, 1 Drawing Sheet

(56) References Cited

U.S. PATENT DOCUMENTS

| | | |
|---|---|---|
| 5,428,024 A | 6/1995 | Chu et al. |
| 5,531,716 A | 7/1996 | Luzio et al. |
| 5,565,519 A | 10/1996 | Rhee et al. |
| 5,571,503 A | 11/1996 | Mausner |
| 5,614,587 A | 3/1997 | Rhee et al. |
| 5,616,568 A | 4/1997 | Pouyani et al. |
| 5,616,611 A | 4/1997 | Yamamoto |
| 5,616,689 A | 4/1997 | Shenoy et al. |
| 5,633,001 A | 5/1997 | Agerup |
| 5,643,464 A | 7/1997 | Rhee et al. |
| 5,676,964 A | 10/1997 | della Valle |
| 5,823,671 A | 10/1998 | Mitchell et al. |
| 5,824,333 A | 10/1998 | Scopelianos et al. |
| 5,827,529 A | 10/1998 | Ono et al. |
| 5,843,907 A | 12/1998 | Sakai |
| 5,880,107 A | 3/1999 | Buenter |
| 5,886,042 A | 3/1999 | Yu et al. |
| 5,935,164 A | 8/1999 | Iversen |
| 5,972,326 A | 10/1999 | Galin et al. |
| 5,972,385 A | 10/1999 | Liu et al. |
| 5,980,930 A | 11/1999 | Fenton et al. |
| 5,985,850 A | 11/1999 | Falk et al. |
| 6,013,679 A | 1/2000 | Kuo et al. |
| 6,066,325 A | 5/2000 | Wallace et al. |
| 6,129,761 A | 10/2000 | Hubbell |
| 6,147,054 A | 11/2000 | Ambrosi |
| 6,224,857 B1 | 5/2001 | Romeo et al. |
| 6,335,035 B1 | 1/2002 | Drizen et al. |
| 6,372,494 B1 | 4/2002 | Naughton et al. |
| 6,383,218 B1 | 5/2002 | Sourdille et al. |
| 6,383,219 B1 | 5/2002 | Telandro et al. |
| 6,387,356 B1 | 5/2002 | Cscrnica |
| 6,418,934 B1 | 7/2002 | chin |
| 6,495,148 B1 | 12/2002 | Abbiati |
| 6,521,223 B1 | 2/2003 | Calias et al. |
| 6,544,503 B1 | 4/2003 | Vanderhoff et al. |
| 6,610,669 B1 | 8/2003 | Calias et al. |
| 6,627,620 B1 | 9/2003 | Nielsen |
| 6,630,486 B1 | 10/2003 | Royer |
| 6,685,963 B1 | 2/2004 | Taupin et al. |
| 6,716,251 B1 | 4/2004 | Asius et al. |
| 6,734,298 B1 | 5/2004 | Barbucci |
| 6,767,924 B2 | 7/2004 | Yu et al. |
| 6,767,928 B1 | 7/2004 | Murphy et al. |
| 6,852,255 B2 | 2/2005 | Yang |
| 6,893,466 B2 | 5/2005 | Trieu |
| 6,903,199 B2 | 6/2005 | Moon |
| 6,921,819 B2 | 7/2005 | Piron et al. |
| 6,924,273 B2 | 8/2005 | Pierce |
| 6,939,562 B2 | 9/2005 | Spiro et al. |
| 6,979,440 B2 | 12/2005 | Shefer et al. |
| 6,991,652 B2 | 1/2006 | Burg |
| 7,015,198 B1 | 3/2006 | Orentreich |
| 7,119,062 B1 | 10/2006 | Alvis et al. |
| 7,129,209 B2 | 10/2006 | Rhee |
| 7,166,570 B2 | 1/2007 | Hunter et al. |
| 7,192,984 B2 | 3/2007 | Berg |
| 7,196,180 B2 | 3/2007 | Aeschlimann |
| 7,214,667 B2 | 5/2007 | Fukuda et al. |
| 7,314,636 B2 | 1/2008 | Caseres et al. |
| 7,316,822 B2 | 1/2008 | Binette |
| 7,491,709 B2 | 2/2009 | Carey |
| 7,635,592 B2 | 12/2009 | West et al. |
| 7,651,702 B2 | 1/2010 | Wang |
| 7,741,476 B2 | 6/2010 | Lebreton |
| 7,767,452 B2 | 8/2010 | Kleinsek |
| 7,799,767 B2 | 9/2010 | Lamberti et al. |
| 7,875,296 B2 | 1/2011 | Binette |
| 7,902,171 B2 | 3/2011 | Reinmuller et al. |
| 8,052,990 B2 | 11/2011 | Hermitte et al. |
| 8,053,423 B2 | 11/2011 | Lamberti et al. |
| 8,124,120 B2 | 2/2012 | Sadozai |
| 8,137,702 B2 | 3/2012 | Binette et al. |
| 8,153,591 B2 | 4/2012 | Masters et al. |
| 8,288,347 B2 | 10/2012 | Collette et al. |
| 8,303,941 B2 | 11/2012 | Musumeci et al. |
| 8,318,695 B2 | 11/2012 | Stroumpoulis et al. |
| 8,338,375 B2 | 12/2012 | Schroeder et al. |
| 8,338,388 B2 | 12/2012 | Lebreton |
| 8,357,795 B2 | 1/2013 | Lebreton |
| 8,394,782 B2 | 3/2013 | Stroumpoulis et al. |
| 8,394,783 B2 | 3/2013 | Stroumpoulis et al. |
| 8,394,784 B2 | 3/2013 | Stroumpoulis et al. |
| 8,455,465 B2 | 6/2013 | Molliard |
| 8,512,752 B2 | 8/2013 | Crescenzi et al. |
| 8,513,216 B2 | 8/2013 | Stroumpoulis et al. |
| 8,524,213 B2 | 9/2013 | Leshchiner et al. |
| 8,563,532 B2 | 10/2013 | Lebreton |
| 8,575,129 B2 | 11/2013 | Bellini |
| 8,586,562 B2 | 11/2013 | Lebreton |
| 8,853,184 B2 | 10/2014 | Strompoulis |
| 8,895,532 B2 | 11/2014 | Bresin et al. |
| 8,945,523 B2 | 2/2015 | Framroze |
| 8,946,192 B2 | 2/2015 | Gousse et al. |
| 9,023,369 B2 | 5/2015 | Malessa et al. |
| 9,662,422 B2 | 5/2017 | Pollock et al. |
| 2001/0039336 A1 | 11/2001 | Miller et al. |
| 2002/0102311 A1 | 8/2002 | Gustavsson et al. |
| 2002/0106793 A1 | 8/2002 | West et al. |
| 2002/0160109 A1 | 10/2002 | Yeo et al. |
| 2003/0031638 A1 | 2/2003 | Joshi et al. |
| 2003/0093157 A1 | 5/2003 | Casares et al. |
| 2003/0096879 A1 | 5/2003 | Fratini et al. |
| 2003/0119985 A1 | 6/2003 | Sehl et al. |
| 2003/0148995 A1 | 8/2003 | Piron et al. |
| 2004/0032058 A1 | 2/2004 | Vang et al. |
| 2004/0101959 A1 | 5/2004 | Marko et al. |
| 2004/0127698 A1 | 7/2004 | Tsai et al. |
| 2004/0127699 A1 | 7/2004 | Zhao et al. |
| 2004/0199241 A1 | 10/2004 | Gravett et al. |
| 2004/0265389 A1 | 12/2004 | Yui et al. |
| 2005/0013729 A1 | 1/2005 | Brown-Skrobot |
| 2005/0025755 A1 | 2/2005 | Hedrick et al. |
| 2005/0101582 A1 | 5/2005 | Lyons et al. |
| 2005/0136122 A1 | 6/2005 | Sadozai et al. |
| 2005/0142152 A1 | 6/2005 | Leshchiner et al. |
| 2005/0181007 A1 | 8/2005 | Hunter |
| 2005/0186261 A1 | 8/2005 | Avelar |
| 2005/0186673 A1 | 8/2005 | Geistlich et al. |
| 2005/0226936 A1 | 10/2005 | Agerup |
| 2005/0266064 A1 | 12/2005 | McCarthy |
| 2005/0271729 A1 | 12/2005 | Wang |
| 2005/0277617 A1 | 12/2005 | Fukuda et al. |
| 2005/0281880 A1 | 12/2005 | Wang |
| 2005/0287180 A1 | 12/2005 | Chen |
| 2006/0029578 A1 | 2/2006 | Hoemann et al. |
| 2006/0040894 A1 | 2/2006 | Hunter et al. |
| 2006/0095137 A1 | 5/2006 | Chung et al. |
| 2006/0105022 A1 | 5/2006 | Yokokawa et al. |
| 2006/0122147 A1 | 6/2006 | Wohlrab |
| 2006/0141049 A1 | 6/2006 | Lyons et al. |
| 2006/0147483 A1 | 7/2006 | Chaouk et al. |
| 2006/0189516 A1 | 8/2006 | Yang |
| 2006/0194758 A1 | 8/2006 | Lebreton |
| 2006/0246137 A1 | 11/2006 | Hermitte et al. |
| 2006/0257346 A1 | 11/2006 | Mohammadi |
| 2006/0257488 A1 | 11/2006 | Hubbard |
| 2006/0286769 A1 | 12/2006 | Tsuchiya et al. |
| 2007/0026070 A1 | 2/2007 | Vonwiller et al. |
| 2007/0036745 A1 | 2/2007 | Leshchiner et al. |
| 2007/0066816 A1 | 3/2007 | Tsai et al. |
| 2007/0077292 A1 | 4/2007 | Pinsky |
| 2007/0104692 A1 | 5/2007 | Quijano et al. |
| 2007/0104693 A1 | 5/2007 | Quijano et al. |
| 2007/0129430 A1 | 6/2007 | Miyata et al. |
| 2007/0178121 A1 | 8/2007 | First et al. |
| 2007/0203095 A1 | 8/2007 | Sadozai et al. |
| 2007/0212385 A1 | 9/2007 | David |
| 2007/0224247 A1 | 9/2007 | Chudzik |
| 2007/0224278 A1 | 9/2007 | Lyons et al. |
| 2007/0298005 A1 | 12/2007 | Thibault |
| 2008/0044476 A1 | 2/2008 | Lyons et al. |
| 2008/0057091 A1 | 3/2008 | Abdellaoui |
| 2008/0081964 A1 | 4/2008 | Zakrzewski |

(56) References Cited

U.S. PATENT DOCUMENTS

| | | |
|---|---|---|
| 2008/0089918 A1 | 4/2008 | Lebreton |
| 2008/0188416 A1 | 8/2008 | Bernstein |
| 2008/0193538 A1 | 8/2008 | Kitazono et al. |
| 2008/0200430 A1 | 8/2008 | Bitterman et al. |
| 2008/0207794 A1 | 8/2008 | Wright et al. |
| 2008/0241252 A1 | 10/2008 | Lyons |
| 2008/0268051 A1 | 10/2008 | Lyons |
| 2008/0274946 A1 | 11/2008 | Gimpapa |
| 2008/0279806 A1 | 11/2008 | Cho |
| 2008/0293637 A1 | 11/2008 | Schroeder et al. |
| 2008/0300681 A1 | 12/2008 | Rigotti et al. |
| 2009/0017091 A1 | 1/2009 | Daniloff et al. |
| 2009/0018102 A1 | 1/2009 | Moutet |
| 2009/0022808 A1 | 1/2009 | Championn |
| 2009/0028817 A1 | 1/2009 | Niklason et al. |
| 2009/0036403 A1 | 2/2009 | Stroumpoulis et al. |
| 2009/0042834 A1 | 2/2009 | Karageozian et al. |
| 2009/0093755 A1 | 4/2009 | Schroeder et al. |
| 2009/0098177 A1 | 4/2009 | Werkmeister et al. |
| 2009/0110671 A1 | 4/2009 | Miyata et al. |
| 2009/0110736 A1 | 4/2009 | Boutros |
| 2009/0123547 A1 | 5/2009 | Hill et al. |
| 2009/0124552 A1 | 5/2009 | Hill et al. |
| 2009/0143331 A1 | 6/2009 | Stroumpoulis et al. |
| 2009/0143348 A1 | 6/2009 | Tezel et al. |
| 2009/0148527 A1 | 6/2009 | Robinson |
| 2009/0155314 A1 | 6/2009 | Tezel |
| 2009/0155362 A1 | 6/2009 | Longin |
| 2009/0162415 A1 | 6/2009 | Huang et al. |
| 2009/0169615 A1 | 7/2009 | Pinsky |
| 2009/0181104 A1 | 7/2009 | Rigotti et al. |
| 2009/0263447 A1 | 10/2009 | Asius et al. |
| 2009/0291986 A1 | 11/2009 | Pappas et al. |
| 2009/0297632 A1 | 12/2009 | Waugh |
| 2009/0317376 A1 | 12/2009 | Zukowska et al. |
| 2010/0004198 A1 | 1/2010 | Stroumpoulis et al. |
| 2010/0028437 A1 | 2/2010 | Lebreton |
| 2010/0028438 A1* | 2/2010 | Lebreton .............. A61K 8/0241 424/488 |
| 2010/0035838 A1 | 2/2010 | Heber et al. |
| 2010/0041788 A1 | 2/2010 | Voigts et al. |
| 2010/0098764 A1 | 4/2010 | Stroumpoulis et al. |
| 2010/0098794 A1 | 4/2010 | Armand |
| 2010/0099623 A1 | 4/2010 | Schroeder et al. |
| 2010/0111919 A1 | 5/2010 | Abuzaina et al. |
| 2010/0136070 A1 | 6/2010 | Dobak et al. |
| 2010/0160948 A1 | 6/2010 | Rigotti et al. |
| 2010/0161052 A1 | 6/2010 | Rigotti et al. |
| 2010/0168780 A1 | 7/2010 | Rigotti et al. |
| 2010/0226988 A1 | 9/2010 | Lebreton |
| 2010/0247651 A1 | 9/2010 | Kestler |
| 2010/0249924 A1 | 9/2010 | Powell et al. |
| 2010/0255068 A1 | 10/2010 | Stroumpoulis et al. |
| 2010/0273747 A1 | 10/2010 | Malessa et al. |
| 2010/0316683 A1 | 12/2010 | Piron |
| 2010/0323985 A1 | 12/2010 | Moutet et al. |
| 2011/0008406 A1 | 1/2011 | Altman et al. |
| 2011/0008436 A1 | 1/2011 | Altman et al. |
| 2011/0008437 A1 | 1/2011 | Altman et al. |
| 2011/0014263 A1 | 1/2011 | Altman et al. |
| 2011/0014287 A1 | 1/2011 | Altman et al. |
| 2011/0020409 A1 | 1/2011 | Altman et al. |
| 2011/0034684 A1 | 2/2011 | Yokokawa |
| 2011/0052695 A1 | 3/2011 | Jiang et al. |
| 2011/0070281 A1 | 3/2011 | Altman |
| 2011/0077737 A1* | 3/2011 | Stroumpoulis ......... A61L 27/20 623/8 |
| 2011/0097381 A1 | 4/2011 | Altman |
| 2011/0104800 A1 | 5/2011 | Kensy et al. |
| 2011/0111031 A1 | 5/2011 | Jiang et al. |
| 2011/0118206 A1 | 5/2011 | Lebreton |
| 2011/0150823 A1 | 6/2011 | Huang |
| 2011/0150846 A1 | 6/2011 | Van Epps |
| 2011/0171286 A1 | 7/2011 | Cecile et al. |
| 2011/0171310 A1 | 7/2011 | Gousse |
| 2011/0171311 A1 | 7/2011 | Gousse et al. |
| 2011/0172180 A1 | 7/2011 | Gousse et al. |
| 2011/0183001 A1 | 7/2011 | Rosson |
| 2011/0183406 A1 | 7/2011 | Kensy |
| 2011/0189292 A1 | 8/2011 | Lebreton |
| 2011/0194945 A1 | 8/2011 | Kensy et al. |
| 2011/0201571 A1 | 8/2011 | Molliard |
| 2011/0224164 A1 | 9/2011 | Lebreton |
| 2011/0229574 A1 | 9/2011 | Guillen et al. |
| 2011/0250276 A1 | 10/2011 | Fournial et al. |
| 2011/0263521 A1 | 10/2011 | Moutet et al. |
| 2011/0295238 A1 | 12/2011 | Kensy et al. |
| 2012/0010146 A1 | 1/2012 | Han et al. |
| 2012/0018959 A1 | 1/2012 | Andersson et al. |
| 2012/0034462 A1 | 2/2012 | Stroumpoulis et al. |
| 2012/0045420 A1 | 2/2012 | Van Epps et al. |
| 2012/0071437 A1 | 3/2012 | Stroumpoulis et al. |
| 2012/0076868 A1 | 3/2012 | Lamberti et al. |
| 2012/0095206 A1 | 4/2012 | Chen |
| 2012/0100217 A1 | 4/2012 | Green |
| 2012/0100611 A1 | 4/2012 | Kensy et al. |
| 2012/0156265 A1 | 6/2012 | Binette et al. |
| 2012/0164098 A1 | 6/2012 | Schroeder et al. |
| 2012/0164116 A1 | 6/2012 | Van Epps |
| 2012/0165935 A1 | 6/2012 | Van Epps |
| 2012/0172328 A1 | 6/2012 | Lebreton |
| 2012/0171265 A1 | 7/2012 | Altman et al. |
| 2012/0172317 A1 | 7/2012 | Altman et al. |
| 2012/0172985 A1 | 7/2012 | Altman et al. |
| 2012/0189589 A1 | 7/2012 | Van Epps et al. |
| 2012/0189590 A1 | 7/2012 | Van Epps et al. |
| 2012/0189699 A1 | 7/2012 | Strompoulis et al. |
| 2012/0189708 A1 | 7/2012 | Van Epps et al. |
| 2012/0190644 A1 | 7/2012 | D'este |
| 2012/0207837 A1 | 8/2012 | Powell et al. |
| 2012/0208890 A1 | 8/2012 | Gousse et al. |
| 2012/0209381 A1 | 8/2012 | Powell et al. |
| 2012/0213852 A1 | 8/2012 | Van Epps et al. |
| 2012/0213853 A1 | 8/2012 | Van Epps et al. |
| 2012/0219627 A1 | 8/2012 | Van Epps et al. |
| 2012/0225842 A1 | 9/2012 | Cecile et al. |
| 2012/0232030 A1 | 9/2012 | Gousse et al. |
| 2012/0263686 A1 | 10/2012 | Van Epps et al. |
| 2012/0265297 A1 | 10/2012 | Altman et al. |
| 2012/0269777 A1 | 10/2012 | Van Epps et al. |
| 2012/0283428 A1 | 11/2012 | Lee et al. |
| 2012/0295870 A1 | 11/2012 | Lebreton |
| 2013/0023658 A1 | 1/2013 | Stroumpoulis et al. |
| 2013/0041038 A1 | 2/2013 | Lebreton |
| 2013/0041039 A1 | 2/2013 | Lebreton |
| 2013/0072453 A1 | 3/2013 | Gousse et al. |
| 2013/0096081 A1 | 4/2013 | Njikang |
| 2013/0116188 A1 | 5/2013 | Pollock et al. |
| 2013/0116190 A1 | 5/2013 | Pollock et al. |
| 2013/0116411 A1 | 5/2013 | Pollock et al. |
| 2013/0123210 A1 | 5/2013 | Liu |
| 2013/0129835 A1 | 5/2013 | Pollock et al. |
| 2013/0131011 A1 | 5/2013 | Lebreton |
| 2013/0131655 A1 | 5/2013 | Rigotti et al. |
| 2013/0136780 A1 | 5/2013 | Tezel et al. |
| 2013/0203696 A1 | 8/2013 | Liu |
| 2013/0203856 A1 | 8/2013 | Cho |
| 2013/0209532 A1 | 8/2013 | Stroumpoulis et al. |
| 2013/0210760 A1 | 8/2013 | Liu |
| 2013/0237615 A1 | 9/2013 | Meunier |
| 2013/0244943 A1 | 9/2013 | Yu et al. |
| 2013/0244970 A1 | 9/2013 | Lebreton |
| 2013/0274222 A1 | 10/2013 | Horne |
| 2013/0287758 A1 | 10/2013 | Tozzi |
| 2014/0011980 A1 | 1/2014 | Chitre et al. |
| 2014/0011990 A1 | 1/2014 | Lebreton |
| 2014/0039061 A1 | 2/2014 | Wiebensjo et al. |
| 2014/0088037 A1 | 3/2014 | Bon Betemps et al. |
| 2014/0227235 A1 | 8/2014 | Kim et al. |

(56) References Cited

U.S. PATENT DOCUMENTS

| | | | |
|---|---|---|---|
| 2015/0151858 A1 | 6/2015 | Turzi | |
| 2017/0273886 A1 | 9/2017 | Gousse | |

FOREIGN PATENT DOCUMENTS

| | | | |
|---|---|---|---|
| CN | 1893989 | 1/2007 | |
| CN | 1902232 | 1/2007 | |
| CN | 1927892 | 3/2007 | |
| CN | 101002725 | 7/2007 | |
| CN | 101432311 | 5/2009 | |
| CN | 101594892 | 12/2009 | |
| CN | 102548590 A | 7/2012 | |
| DE | 20221171 | 6/2005 | |
| EP | 0273823 | 7/1988 | |
| EP | 0416250 | 3/1991 | |
| EP | 0416846 | 3/1991 | |
| EP | 0637450 | 2/1995 | |
| EP | 1247522 | 10/2002 | |
| EP | 1419792 | 4/2003 | |
| EP | 1398131 | 3/2004 | |
| EP | 1115433 | 12/2004 | |
| EP | 1532991 | 5/2005 | |
| EP | 1726299 | 11/2006 | |
| EP | 1932530 A1 | 6/2008 | |
| EP | 2236523 | 10/2010 | |
| EP | 2484387 | 8/2012 | |
| EP | 2670447 | 7/2015 | |
| EP | 2676658 | 9/2015 | |
| FR | 2733427 | 10/1996 | |
| FR | 2752843 | 3/1998 | |
| FR | 2873379 | 5/2008 | |
| FR | 2920000 | 2/2009 | |
| FR | 2924615 | 6/2009 | |
| JP | 55-153711 | 11/1980 | |
| JP | S 61-500500 | 3/1986 | |
| JP | S 62-293177 | 12/1987 | |
| JP | H 07-191022 | 7/1995 | |
| JP | 2002-020259 | 1/2002 | |
| JP | 2002080501 | 3/2002 | |
| JP | 2003-522255 | 7/2003 | |
| JP | 2006-208386 | 8/2006 | |
| JP | 2007-043960 | 1/2007 | |
| JP | 2007063177 | 3/2007 | |
| JP | 2009-535453 | 10/2009 | |
| JP | 2010-535277 | 11/2010 | |
| JP | 2011-505362 | 2/2011 | |
| KR | 2006-0008906 | 1/2006 | |
| KR | 2010-0046038 | 5/2010 | |
| KR | 20110138765 | 12/2011 | |
| KR | 20130018518 | 2/2013 | |
| RU | 2363496 | 8/2009 | |
| WO | 1986000079 | 1/1986 | |
| WO | 1986000912 | 2/1986 | |
| WO | WO 91/04058 | 4/1991 | |
| WO | 1992000105 | 1/1992 | |
| WO | 1992020349 | 11/1992 | |
| WO | 1994001468 | 1/1994 | |
| WO | 1994002517 | 2/1994 | |
| WO | 1996033751 | 1/1996 | |
| WO | 1997004012 | 2/1997 | |
| WO | WO 97/004012 | 6/1997 | |
| WO | 1998035639 | 8/1998 | |
| WO | 1998035640 | 8/1998 | |
| WO | WO 98/035639 | 8/1998 | |
| WO | WO 98/035640 | 8/1998 | |
| WO | WO 99/50258 | 10/1999 | |
| WO | 2000001428 | 1/2000 | |
| WO | 2000008061 A1 | 2/2000 | |
| WO | WO 00/46252 | 8/2000 | |
| WO | WO 01/058961 | 8/2001 | |
| WO | 2001079342 | 10/2001 | |
| WO | 2002005753 | 1/2002 | |
| WO | 2002006350 | 1/2002 | |
| WO | 2002009792 | 2/2002 | |
| WO | 2002017713 | 3/2002 | |
| WO | 2003007782 | 1/2003 | |
| WO | 2004020473 | 3/2004 | |
| WO | 2004022603 | 3/2004 | |
| WO | 2004067575 A1 | 8/2004 | |
| WO | WO2004067575 | 8/2004 | ............ C08B 37/08 |
| WO | 204073759 | 9/2004 | |
| WO | 2004092223 | 10/2004 | |
| WO | 2005040224 | 5/2005 | |
| WO | WO 2005/052035 | 6/2005 | |
| WO | 2005067944 | 7/2005 | |
| WO | 2005074913 | 8/2005 | |
| WO | 2005112888 | 12/2005 | |
| WO | WO 2006/015490 | 2/2006 | |
| WO | WO 2006/020994 | 2/2006 | |
| WO | 2006023645 | 3/2006 | |
| WO | WO2006021644 A1 | 3/2006 | |
| WO | 2006048671 | 5/2006 | |
| WO | 2006056204 | 6/2006 | |
| WO | 2006067608 | 6/2006 | |
| WO | WO 2007/004300 | 1/2007 | |
| WO | 2007018124 | 2/2007 | |
| WO | 2007070617 | 6/2007 | |
| WO | 2007077399 | 7/2007 | |
| WO | 2007128923 | 11/2007 | |
| WO | 2007136738 | 11/2007 | |
| WO | WO 2007/127277 | 11/2007 | |
| WO | 2008015249 A2 | 2/2008 | |
| WO | 2008034176 | 3/2008 | |
| WO | WO 2008/063569 | 5/2008 | |
| WO | 2008068297 | 6/2008 | |
| WO | 2008072230 | 6/2008 | |
| WO | 2008077172 | 7/2008 | |
| WO | WO 2008/078154 | 7/2008 | |
| WO | 2008098019 | 8/2008 | |
| WO | 2008139122 | 11/2008 | |
| WO | WO 2008/140665 | 11/2008 | |
| WO | 2008148967 | 12/2008 | |
| WO | 2008157608 | 12/2008 | |
| WO | WO 2008/148071 | 12/2008 | |
| WO | WO 2009/003135 | 12/2008 | |
| WO | 2009024350 A2 | 2/2009 | |
| WO | 2009024719 | 2/2009 | |
| WO | 2009026158 | 2/2009 | |
| WO | WO 2009/018076 | 2/2009 | |
| WO | WO 2009/024677 | 2/2009 | |
| WO | 2009028764 | 3/2009 | |
| WO | 2009034559 | 3/2009 | |
| WO | 2009073437 | 6/2009 | |
| WO | 2010003797 | 1/2010 | |
| WO | WO 2010/003104 | 1/2010 | |
| WO | 2010027471 | 3/2010 | |
| WO | 2010028025 | 3/2010 | |
| WO | 2010029344 | 3/2010 | |
| WO | WO 2010/026299 | 3/2010 | |
| WO | 2010038771 | 4/2010 | |
| WO | 2010051641 | 5/2010 | |
| WO | 2010052430 | 5/2010 | |
| WO | 2010053918 | 5/2010 | |
| WO | 2010061005 | 6/2010 | |
| WO | 2010015900 | 2/2011 | |
| WO | WO2011023355 A2 | 3/2011 | |
| WO | WO 2011/059909 | 5/2011 | |
| WO | WO 2009/073508 | 6/2011 | |
| WO | WO 2011/068303 | 6/2011 | |
| WO | WO 2011/072399 | 6/2011 | |
| WO | WO 2011/086458 | 7/2011 | |
| WO | 2011135150 | 11/2011 | |
| WO | 2012008722 | 1/2012 | |
| WO | 2012/077055 | 6/2012 | |
| WO | WO 2012/104419 | 8/2012 | |
| WO | WO 2012/167079 | 12/2012 | |
| WO | WO 2013/040242 | 3/2013 | |
| WO | WO2013040242 A2 | 3/2013 | |
| WO | WO 2013/067293 | 5/2013 | |
| WO | 2013086024 A2 | 6/2013 | |
| WO | WO 2014/026161 | 2/2014 | |

(56) References Cited

FOREIGN PATENT DOCUMENTS

| | | |
|---|---|---|
| WO | WO 2014/032804 | 3/2014 |
| WO | WO 2014/076929 | 5/2014 |

OTHER PUBLICATIONS

Santoro, S. et al., J. Appl. Biomater. Biomech., "Rheological properties of cross-linked hyaluronic acid dermal fillers", 2011, vol. 9, No. 2, pp. 127-136 (Year: 2011).*
Laeschke, "Biocompatibility of Microparticles into Soft Tissue Fillers", 23 Semin. Cutan. Med. Surg., 214 (2004).
Lamar et al., "Antifibrosis Effect of Novel Gels in Anterior Ciliary Sclerotomy ACS)," ARVO 2002 abstract.
Levy, Jaime et al., "Lidocaine hypersensitivity after subconjunctival injection", Can J Ophthaimol 2006; 41:204-6.
Lindvall et al.; "Influence of Various Compunds on the Degradation of Hyaluronic Acid by a Myeloperoxidase System"; Chemico-Biological Interactions; vol. 90; pp. 1-12; 1994.
Lupo, MP., "Hyaluronic acid fillers in facial rejuvenation." Semin. Cutan. Med. Surg. 25(3): 122-126 (2006).
Mackley, et al., "Delayed-Type Hypersensitivity to Lidocaine", Arch Dermatol, vol. 139, Mar. 2003, pp. 343-346.
Mancinelli et al., "Intramuscular High-Dose Triamcinolone Acetonide in the Treatment of Severe Chronic Asthma" West J. Med, Nov. 1997; 167(5), 322-329.
Matsumoto, Alan H, et al., "Reducing the Discomfort of Lidocaine Administration through pH Buffering," Journal of Vascular and Interventional Radiology, Jan.-Feb. 1994, pp. 171-175.
McCarty et al., "Inflammatory Reaction After Intrasynovial Injection of Microcrystalline Adrenocorticosteroid Esters", Arthritis and Rheumatism, 7(4):359-367 (1964).
McCleland; Plastic Reconstructive Surgery, 100(6), Nov. 1997, pp. 1466-1474.
McPherson, John M., "Development and Biochemical Characterization of Injectable Collagen," J. Dermatol Surg Oncol, 14 (Suppl 1):Jul. 7, 1988, pp. 13-20.
Millay et al.; "Vasoconstrictors in Facial Plastic Surgery"; Archives of Otolaryngology—Head & Neck Surgery; vol. 117; pp. 160-163; Feb. 1991.
Orvisky, E., et al, "High-molecular-weight hyaluronan—a valuable tool in testing the antioxidative activity of amphiphilic drugs stobadine arid vinporetine," Pharm.Biomed.Anal. 16:419-424 (1997).
Osmitrol (generic name Mannitol),Official FDA Information, side effects and uses, pp. 1-10 (2010) http://www.drugs.com/pro/osmitrol.html.
Park et al., "Biological Characterization of EDC-crosslinked Collagen-Hyaluronic Acid Matrix in Dermal Tissue Restoration", Biomaterials 24 (2003) 1631-1641.
Park et al., "Characterization of Porous Collagen/Hyaluronic Acid Scaffold Modified by 1-ethyl-3-(3-dimethylaminopropyl)carbodiimide cross-linking", Biomaterials 23 (2002): 1205-1212.
Powell; "Stability of Lidocaine in Aqueous Solution: Effect of Temperature, pH, Buffer, and Metal Ions on Amide Hydrolysis"; Pharmaceutical Research; vol. 4, No. 1, 1987.
Prestwich, Glenn D., "Evaluating drug efficacy and toxicology in three dimensions: using synthetic extracellular matrices in drug discovery," Accounts of Chemical Research 41 (1):139-148 (2008).
Rehakova, Milena, et al., "Properties of collagen and hyaluronic acid composite materials and their modifications by chemical crosslinking," Journal of Biomedical Research, vol. 30, 1996, pp. 36-372, XP002590342.
Remington's Pharmaceutical Science Mac Publishing Company, Easton, PA 16th Edition 1980.
Rosenblatt et al., "The Effect of Collagen Fiber Size Distribution on the Release Rate of Proteins from Collagen Matrices by Diffusion", J. Controlled Rel., 9, pp. 195-203 (1989).
Rosenblatt et al., "Chain Rigidity and Diffusional Release in Biopolymer Gels", Proceed. Inter. Symp. Control. Rel. Bioact. Mater., 20, pp. 264-265 (1993) Controlled Release Society, Inc.
Sannino et al., "Crosslinking of Cellulose Derivatives and Hyaluronic Acid with Water-Soluble Carbodiimide," Polymer 46 (2005)pp. 11206-11212.
Sculptra® Aesthetic (injectable poly-L-lactic acid) Directions for Use, Dermik Laboratories product insert (Jul. 2009), sanofi-aventis U.S. LLC.
Segura et al. "Crosslinked hyaluronic acid hydrogels: a strategy to functionalize and pattern." Biomaterials 26(4):359-371 (2005).
Selvi et al, "Arthritis Induced by Corticosteroid Crystals", J. Rheumatology, 2004, 34:3.
Serban et al. "Modular Extracellular Matrices: Solutions for the Puzzle." Methods 45(1): 93-98 (2008).
Shu et al. "Synthesis and evaluation of injectable, in situ crosslinkable synthetic extracellular matrices for tissue engineering." J. Biomed. Mater. Res. A. 79(4): 902-912 (2006).
Silver et al., "Physical Properties of Hyaluronic Acid and Hydroxypropylmethylcellulose in Solution: Evaluation of Coating Ability," Journal of Applied Biomaterials, vol. 5, 89-98 (1994).
Skardal etal "Bioprinting Vessel-Like Constructs Using Hyaluronan Hydrogels Crosslinkedwith Tetrahedral Polyethylene Glyol Tetracrylates"; BioMaterials. Elsevier Science Publishers BV; vol. 31, No. 24; pp. 6173-6181; Aug. 1, 2010.
Smith, Kevin C., et al., "Five Percent Lidocaine Cream Applied Simultaneously to Skin and Mucosa of the Lips Creates Excellent Anesthesia for Filler Injections", Dermatol Surg 2005; 31:1635-1637.
Tezel et al. "The science of hyaluronic acid dermal fillers." J. Cosmet. Laser Ther. 10(1): 35-42 (2008).
TRB Chemedica Ophthalmic Line, Visiol, product info., pp. 1-2.
Visiol, Viscoelstic gel for use in ocular surgery, (2010) p. 1, htt://www.trbchemedica.com/index.php/option=com_content&tas.
Waraszkiewicz, Sigmund M., et al., "Stability-Indicating High-Performance Liquid Chromatographic Analysis of Lidocaine Hydrochloride and Lidocaine Hydrochloride with Epinephrine Injectable Solutions", Journal of Pharmaceutical Sciences, vol. 70, No. 11, Nov. 1981, pp. 1215-1218.
Wahl, "European Evaluation of a New Hyaluronic Acid Filler Incorporating Lidocaine", Journal of Cosmetic Dermatology; vol. 7; pp. 298-303; 2008.
Weidmann; "New Hyaluronic Acid Filler for Subdermal and Long-Lasting Volume Restoration of the Face"; European Dermatology; pp. 65-68; 2009.
Xia, Yun et al., "Comparison of Effects of Lidocaine Hydrochloride, Buffered Lidocaine, Diphenhydramine, and Normal Saline After Intradermal Injection", Journal of Clinical Anesthesia 14:339-343, 2002.
Yeom et al. "Effect of Cross-Linking Reagents for Hyaluronic Acid Hydrogel Dermal Fillers on Tissue Augmentation and Regeneration." Bioconjugate Chem., 21(2): 240-247 (2010).
Yui, Nobuhiko, et al., "Inflammation responsive degradation of crosslinked hyaluronic acid gels," Journal of Controlled release, 22 (1992) pp. 105-116.
Yui, Nobuhiko, et al., "Photo-responsive degradation of heterogeneous hydrogels comprising crosslinked hyaluronic acid and lipid microspheres for temporal drug delivery," Journal of Controlled Release, 26 (1993) pp. 141-145.
Yun, YH et al. "Hyaluronan Microspheres for Sustained Gene Delivery and Site-Specific Targeting", Biomaterials, vol. 25, 2004, pp. 147-157.
Zheng et al. "In situ crosslinkable hyaluronan hydrogels for tissue engineering." Biomaterials 25(7-8): 1339-1348 (2004).
Zulian et al., Triamcinolone Acetonide and Hexacetonide Intra-Articular Treatment of Symmetrical Joints in Juvenile Idiopathic Arthritis: a Double-Blind Trial, Rheum 2004.
Boulle et al., "Lip Augmentation and Contour Correction With a Ribose Cross-linked Collagen Dermal Filler", Journals of Drugs in Dermatology, Mar. 2009, vol. 8, Issue 3, pp. 1-8.
Crosslinking Technical Handbook, Thermo Scientific, pp. 1-48, published Apr. 2009.
Park et al., "In vireio evaluation of conjugated Hyalruonic acid with Ascorbic Acid", Journal of Bone & Joint Surgery, British vol. 92-B, XP-002706399, 2010.

(56) References Cited

OTHER PUBLICATIONS

Aestetic Buyers Guide, "Juvéderm Raises Standards" Jan./Feb. 2007 (5 pp.), www.miinews.com.
Adams, "An Analysis of Clinical Studies of the Uses of Crosslinked Hyaluronan, Hylan, in the Treatment of Osteoarthritis", J. Rheumatol. Suppl., Aug. 1993; 39:16-8.
Albano, Emanuele, et al., "Hydroxyethyl Radicals in Ethanol Hepatotoxicity," Frontiers in Bioscience 4:533-540 (1999).
Allemann et al., "Hyaluronic acid gel (Juvederm) preparations in the treatment of facial wrinkles and folds", 2008, Clinical Interventions in Aging, vol. 3, No. 4, pp. 629-634.
Antunes, Alberto A., et al., "Efficacy of Intrarectal Lidocaine Hydrochloride Gel for Pain control in Patients Undergoing Transrectal Prostate Biopsy", International Braz J Urol, vol. 30(5): 380-383, Sep.-Oct. 2004.
Atanassoff, Peter G., et al., "The Effect of Intradermal Administration of Lidocaine and Morphine on the Response to Thermal Stimulation", Anesth Analg 1997; 84:1340-3.
Baumann et al. "Juvederm vs. Zyplast Nasolabial Fold Study Group, Comparison of smooth-gel hyaluronic acid dermal fillers with cross-linked bovine collagen: a multicenter, double-masked, randomized, within-subject study." Dermatol. Surg. 33(Suppl 2): S128-S135 (2007).
Beasley et al. :Hyaluronic acid fillers: a comprehensive review. Facial Plast. Surg. 25(2): 86-94 (2009).
Beer "Dermal fillers and combinations of fillers for facial rejuvenation." Dermatol. Clin. 27(4): 427-432 (2009).
Beide, Jose I., et al., "Hyaluronic acid combined with mannitol to improve protection against free-radical endothelial damage: Experimental Model," J.Cataract Refract Surg 2005; 31:1213-1218.
Bircher, Andreas J., et al., "Delayed-type hypersensitivity to subcutaneous lidocaine with tolerance to articaine: confirmation by in vivo and in vitro tests", Contact Dermatitis 1996, 34, 387-389.
Bluel et al., "Evaluation of Reconstituted Collagen Tape as a Model for Chemically Modified Soft Tissues", Biomat. Med. De. Art. Org., 9(1):37-46 (1981).
Buck et al, "Injectable Fillers for our Facial Rejuvenation: a Review", Journal of Plastic, Reconstructive and Aesthetic Surgery, (2009), 62:11-18, XP002668828.
Capozzi et al., "Distant Migration of Silicone Gel From a Ruptured Breats Implant", Plastic and Reconstructive Surgery, 1978; 62:302-3.
Carlin, G., et al., "Effect of anti-inflammatory drugs on xanthine oxidase and xanthine oxidase induced depolymerization of hyaluronic acid," Agents and Actions. 16 (5):377-384 (1985).
Carruthers et al. "The science and art of dermal fillers for soft-tissue augmentation." J. Drugs Dermatol. 8(4): 335-350 (2009).
Champion, et al., "Role of Target Geometry in Phagocytosis", S. Proc. Nat. Acad. Sci., Mar. 2008, 2006, vol. 103, No. 13, pp. 4930-4934.
Chin, Thomas M., et al., "Allergic Hypersensitivity to Lidocaine Hydrochloride", International journal of Dermatology, vol. 19, Apr. 1980, pp. 147-148.
Chvapil, "Collagen Sponse: Theory and Practice of Medical Applications", J. Biomed Mater. Res., II, pp. 721-741 (1977).
Clark et al., "The Influence of Triamcinolone Acetonide on Joint Stiffness in the Rat", J Bone Joint Surg Am, 1971; 53:1409-1414.
Cohen et al., "Organization and Adhesive Properties of the Hyaluronan Pericellular Coat of Chondrocytes and Epithelial Cells", Biophys J., 2003; 85:1996-2005.
Cui et al; "The Comparison of Physicochemical Properties of Four Cross-Linked Sodium Hyaluronate Gels with Different Cross-Linking Agents"; Advanced Material Research; vols. 396-398; pp. 1506-1512; 2012.
Deland, "Intrathecal Toxicity Studies with Benzyl Alcohol", Toxicol Appl Pharmacol, 1973; 25(2):153.
Desai et al., J Pharm Sci Feb. 1995; 84 (2): 212-5.
Eyre et al., Top Curr. Chem., 2005, vol. 247, pp. 207-229.

Falcone et al. "Crosslinked hyaluronic acid dermal fillers: a companson of rheological properties." J Biomed Mater Res A. 87(1): 264-271 (2008).
Falcone et al. "Temporary polysaccharide dermal fillers: a model for persistence based on physical properties." Dermatol Surg. 35(8): 1238-1243 (2009).
Farley, Jon S., et al., "Diluting Lidocaine and Mepivacaine in Balanced Salt Solution Reduces the Pain of Intradermal Injection", Regional Anesthesia 19(1):48-51, 1994.
Frati, Elena, et al., "Degradation of hyaluronic acid by photosensitized riboflavin in vitro. Modulation of the effect by transition metals, radical quenchers, and metal chelators," Free Radical Biology Medicine 22 (7):1139-1144 (1997).
Fujinaga, Masahiko, et al., "Reproductive and Teratogenic Effects of Lidocaine in Sprague-Dawley Rats", Anesthesiology 65:626-632, 1986.
Gammaitoni, Arnold R., et al., "Pharmacokinetics and safety of continuously applied lidocaine patches 5%", Am J Health Syst Pharm, vol. 59, Nov. 15, 2002, pp. 2215-2220.
GinShiCel MH Hydroxy Propyl methyl Cellulose, Web Page http://www.ginshicel.cn/MHPC.html, Nov. 12, 2008.
Gold MH, "Use of Hyaluronic acid fillers for the treatment of the aging face." Clin. Interventions Aging 2(3):369-376 (2007).
Goldberg "Breakthroughs is US dermal fillers for facial soft-tissue augmentation." J Cosmet Laser Ther. 11(4): 240-247 (2009).
Graefe, Hendrik, et al., "Sensitive and specific photometric determination of mannitol in human serum," Clin Chem Lab Med. 41 (8):1049-1055 (2003).
Grecomoro et al., "Intra-Articular Treatment with Sodium Hyaluronate in Gonarthosis " A Controlled Clinical Trial Versus Placebo, Pharmatherapeutica, 1987; 5(2):137-41.
Grillo et al., "Thermal Reconstitution of Collagen from Solution and the Response to Its Heterologous Implantation", JSR II, No. 1, pp. 69-82 (1962).
Hassan et al., Effects of Adjuvants to local anaesthetics on their duration. III. Experimental studies of hyaluronic acid. Abstract Pub Med [Acta Anesthesiol Scand. May 1985; 29(4):384-8].
Hayashibara, "AA2G"; Sep. 23, 2007, http://web.archive.org/web/2007973072010/http://www.hayashibara-intl.com/cosmetics/aa2g.html.
Helary et al., "Concentrated collagen hydrogels as dermal substitutes", Biomaterials 31 (2010) 481-490.
Helliwell, "Use of an Objective Measure of Articular Stiffness to Record Changes in Finger Joints After Intra-Articular Injection of Corticosteroid", An Theum Dis, 1997; 56:7.
Hertzberger-Ten et al., "Intra-Articular Steroids in Pauciarticular Juvenile Chronic Arthritis", Type I, Eur J Ped 1991; 150:170-172.
Hetherington, "Potential for Patient Harm From Intrathecal Administration of Preserved Solutions", Med J Aust, 2000, 173(3):p. 141.
Hurst, "Adhesive Arachnoiditis and Vascular Blockage Caused by Detergents and Other Chemical Irritants: an Experimental Study", J Path Bact, 1955; 70:167.
Intramed Mannitol 20% m/v Infusion, package insert, pp. 1-2 (2010) http://home.intekom.com/pharm/intramed/manitl20.html.
Jones et al., "Intra-Articular Hyaluronic Acid Compared to Intra-Articular Triamcinolone Hexacetonide in Inflammatory Knee Osteoarthritis", Osteoarthritis Cartilage, 1995, 3:269-273.
Kablik et al. "Comparative physical properties of hyaluronic acid dermal fillers." Dermatol. Surg. Suppl. 35(Suppl. 1): 302-312 (2009).
Klein, "Skin Filling Collagen and Other Injectables of the Skin", Dermatologic Clinics, Jul. 2001, vol. 19, No. 3, pp. 491-588, ix, XP00919589.
Kopp et al., The Short-Term Effect of Intra-Articular Injections of Sodium Hyaluronate and Corticosteroid on Temporomandibular Joint Pain and Dysfunction, J. Oral Maxillofac.
Kulicke et al., "Visco-Elastic Properties of Sodium Hyaluronate Solutions," American Institue of Physics (2008).
18840 European Patent Applicaton No. 12799706.2-1458, Office Action, dated Aug. 1, 2014.

(56) References Cited

OTHER PUBLICATIONS

Jeon, Oju et al., Mechanical Properties and Degradation Behaviors of Hyaluronic Acid Hydrogels Cross-Linked at Various Cross-Linked Densitiies, Carbonhydrate Polymers, 2007, 251-257, vol. 70, XP022241928.

Junseok, Yeom et al, Effect of Cross-Linking Reagents for Hyaluronic Acid Hydrogel Dermal Fillers on Tissue Agumentaiton and Registration, Bioconjugate Chemistry, vol. 21, No. 2, Feb. 17, 2010, pp. 240-247, XP055045386.

Park, D.J. et al., In Vitro Evalutation of Conjugated Hyaluronic Acid with Ascorbic Acid, J. Bone Joint Surg., British vol. 2010, Retrieved from the internet: http://www.bjjprocs.boneandjoint.org.uk/content/92-B/SUPP I/115.3.abstract [retrieved on Jul. 29, 2013] abstract XP002706399.

International Application No. PCT/US2012/067993, International Search Repot, Written Opinion of the International Search Authority, and International Preliminary Report on Patentability Chapter I, dated May 27, 2014.

Kablik et al., Dermatologic Surgery, "Comparative Physical Properties of Hayluronic Acid Dermal Fillers", Feb. 2009, vol. 35, s1, pp. 302-312.

Borrell, Marcos et al., Lift capabilities of hyaluronic acid fillers, Journal of Cosmetic and Laser Therapy, 2011; 21-27: 13, Informa UK, Ltd.

Reply under 37 CFR 1.111, U.S. Appl. No. 13/706,221, dated May 2, 2016, Prosecution History,, 13 pages.

Tomihata, Kenji et al., Crosslinking of Hyaluronic Acid with Water-Soluable Carbodiimide, J. Biomed Mater Res., 1997, vol. 37(2), pp. 243-251.

Bergman et al., "Hyaluronic Acid Derivatives Prepared in Aqueous Media by Triazine-Activated Amidation," Biomacromolecules, 2007, 8, 2190-2195.

Bulpitt et al., "New strategy for chemical modification of hyaluronic acid: Preparaton of functionalized derivatives and their use in the formation of novel biocompatible hydrogels," Journal of Biomedical Materials Research, vol. 4 7, No. 2, Jan. 1, 1999, pp. 153-169.

Di Meo et al., "Synthesis and NMR Characterization of New Hyaluronan-Based NO Donors," Biomacromolecules, 2006, 7, 1253-1260.

Kuo et al., "Chemical Modification of Hyaluronic Acid by Carbodiimides," Bioconjugate Chem., 1991, 2, 232-241.

Magnani et al., "Novel Polysaccharide Hydrogels: Characterization and Properties," Polymers for Advanced Technologies, 11, 488-495 (2000).

Yan et al., "Improved synthesis of hyaluronic acid hydrogel and its effect on tissue augmentation," Journal of Biomaterials Applications, 0(0) 1-9, 2011.

Edwards et al., Review of long-term adverse effects associated with the use of chemically-modified animal and nonanimal source hyaluronic acid dermal fillers, Clinical Interventions in Aging, 2007, 509-519, 2(4), Dove Medical Press Limited.

Okay, O., General Properties of Hydrogels: Hydrogel Sensors and Actuators, Springer Series on Chemical Sensors and Biosensors, 2009, pp. 1-14, 6, Springer-Verlag Berlin Heidlberg.

Wende, Frida J. et al., 1D NMR Methods for Determination of Degree of Cross-Linking and BDDE Substitution Positions in HA Hydrogels, Carbohydrate Polymers, 2017, pp. 1525-1530, 157.

Nadim et al., "Improvement of polyphenol properties upon glucosylation in a UV-induced skin cell ageing model," Sep. 2014, International Journal of Cosmetic Science, vol. 36, No. 6, pp. 579-587.

National Center for Biotechnology Information, PubChem Compound Database, CID=370, 2018, https://pubchem.ncbi.nim.nih.gov/compound/370.

National Center for Biotechnology Information, PubChem Compound Database, CID=689043, 2018, https://pubchem.ncbi.nim.nih.gov/compound/689043.

Aesthetic Buyers Guide, "Juvederm Raises Standards," Jan./Feb. 2007, 5 pages, www.miinews.com.

Belda et al., "Hyaluronic Acid Combined With Mannitol to Improve Protection Against Free-Radical Endothelial Damage: Experimental Model," J Cataract Refract Surg, 2005, vol. 31, pp. 1213-1218.

Berezovsky, V.M., 1973.

Bluel et al., "Evaluation of Reconstituted Collagen Tape as a Model for Chemically Modified Soft Tissues," Biomat. Med. Dev. Art. Org., 1981, vol. 9, No. 1, pp. 37-46.

Brandt et al., Clinical Interventions in Aging, "Hyaluronic acid gel fillers in the management of facial aging", 2008: 3(1), pp. 153-159.

Choi et al., "A novel L-ascorbic acid and peptide conjugate with increased stability and collagen biosynthesis," BMB Reports, 2009, vol. 42, No. 11, pp. 743-746.

Chvapil, "Collagen Sponge: Theory and Practice of Medical Applications," J. Biomed. Mater. Res., 1977, vol. 11, pp. 721-741.

Cohen et al., "Organization and Adhesive Properties of the Hyaluronan Pericellular Coat of Chondrocytes and Epithelial Cells," Biophysical Journal, 2003, vol. 85, pp. 1996-2005.

Davidenko et al., "Collagen-hyaluronic acid scaffolds for adipose tissue engineering," Acta Biomaterialia, 2010, vol. 8, pp. 3957-3968.

Edwards et al., "Review of long-term adverse effects associated with the use of chemically-modified animal and nonanimal source hyaluronic acid dermal fillers", Clinical Interventions in Aging, 2007: 2(4), pp. 509-519.

Goldberg, "Breakthroughs in US dermal fillers for facial soft-tissue augmentation," Journal of Cosmetic and Laser Therapy, 2009, vol. 11, pp. 240-247.

Grillo et al., "Thermal Reconstitution of Collagen From Solution and the Response to Its Heterologous Implantation," JSR, 1962, vol. 2, No. 1, pp. 69-82.

Igaku no ayumi, "Rejuvenation of the aging skin," 2005, vol. 215, No. 2, p. 145-148.

Intramed (PTY) LTD, Intramed Mannitol 20% m/v Infusion, Package Insert, Jan. 1979, 2 pages.

Jeon, "Mechanical properties and degradation behaviors of hyaluronic acid hydrogels cross-linked at various cross-linking densities", Carbohydrate Polymers, Applied Science Publishers, Ltd. Barking, GB., vol. 70, No. 3, Sep. 11, 2007, pp. 251-257.

Kim et al., "Gallotannin Isolated from Euphorbia Species, 1, 2, 6-Tri-O-galloyl-b-D-allose, Decreases Nitric Oxide Production through Inhibition of Nuclear Factor-K>B and Downstream Inducible Nitric Oxide Synthase Expression in Macrophages," Jun. 2009, Biological and Pharmaceutical Bulletin, vol. 32, No. 6, pp. 1053-1056.

Lemperele et al., "A Classification of Facial Wrinkles," Plastic and Reconstructive Surgery, Nov. 2001, vol. 108, vol. 6, pp. 1735-1750.

Meves, "Vitamin C Derivative Ascorbyl Palmitate Promotes Ultraviolate-B-Induced Lipid Peroxidation and Cytotoxicity in Keratinocytes", Journal of Investigative Dermatology, vol. 119, No. 5, Nov. 2002. pp. 1103-1108.

Nayama et al., "Protective Effects of Sodium-L-ascorbyl-2 Phosphate on the Development of UVB-induced Damage in Cultured Mouse Skin," Biol. Pharm. Bull., 1999, vol. 22, No. 12, pp. 1301-1305.

Patterson et al. Biomaterials, "Hyaluronic acid hydrogels with controlled degradation properties for oriented bone regeneration", 2010, vol. 31 pp. 6772-6781.

Silver et al., "Physical Properties of Hyaluronic Acid and Hydroxypropylmethylcellulose in Solution: Evaluation of Coating Ability," Journal of Applied Biomaterials, 1994, vol. 5, pp. 89-98.

Skardal et al., "Bioprinting Vessel-Like Constructs Using Hyaluronan Hydrogels Crosslinked With Tetrahedral Polyethylene Glycol Tetracrylates," Biomaterials, 2010, vol. 31, pp. 6173-6181.

Sureshabu et al., Amino Acids, Peptides and Proteins in Organic Chemistry, "Chapter 1: Protection Reactions", vol. 4, published online Apr. 2011, pp. 1-97.

Takamizawa et al. Cell Biology International, "Effects of ascorbic acid and ascorbic acid 2-phosphate, a long-acting vitamin C derivative, on the proliferation and differentiation of human osteoblast-like cells", 2004, vol. 28, pp. 255-265.

Visiol, TRB Chemedica Ophthalmic Line, Product Info, May 2014, p. 1-2, Geneva, CH.

(56) References Cited

OTHER PUBLICATIONS

Wende, "1D NMR methods for determination of degree of cross-linking and BDDE substitution positions in HA hydrogels", Carbohydrate Polymers, vol. 157, pp. 1525-1530, 2017.

Xuejun et al., "Preparation and Characterization of a Hydrogel from Low-molecular Weight Hyaluronic Acid," Journal of Bioactive and Compatible Polymers, 2004, vol. 19, pp. 5-15.

Yun et al., "Hyaluronan Microspheres for Sustained Gene Delivery and Site-Specific Targeting," Biomaterials, 2004, vol. 25, pp. 147-157.

Zheng et al., "In situ crosslinkable hyaluronan hydrogels for tissue engineering," Biomaterials, 2004, vol. 25, pp. 1339-1348.

Zulian et al., "Triamcinolone acetonide and hexacetonide intra-articular treatment of symmetrical joints in juvenile idiopathic arthritis: a double-blind trial," Rheumatology, Oct. 2004, vol. 43, No. 10, pp. 1288-1291.

Pierre, et al., "Basics of Dermal Filler Rheology," Dermatol Surg, 2015, vol. 41, pp. S120-S126.

Juvederm Volux, Product Insert, Jul. 26, 2018, 65 pages.

Park, "Conjugation of Hyaluronic Acid With Ascorbic Acid and Evaluation of its in Vitro Activity on MC3T3-E1," Master's Thesis, Yonsei University, Dec. 2008, 58 pages.

\* cited by examiner

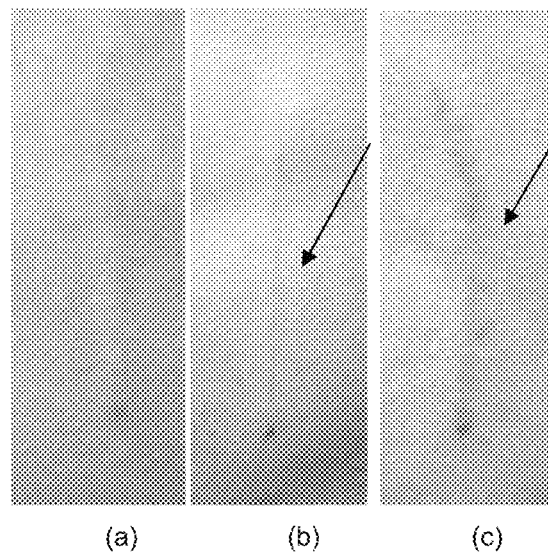
Figure 1. Images of gels in skin from (a) Example 8 of the invention, (b) Commercial Fine Line Filler I, and (c) Commercial Fine Line Filler II
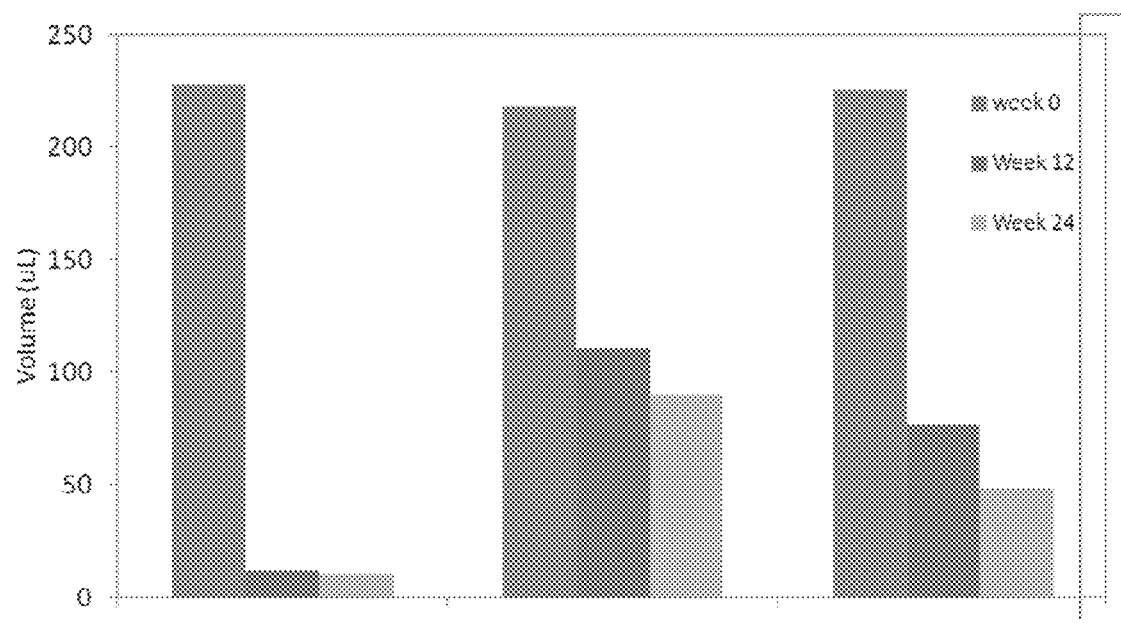
Figure 2. Overall volume of gel remaining after 24 week implantation of gels in made according to Examples 8 and 9, with Commercial Fine Line Filler III, as control

DERMAL FILLER COMPOSITIONS

RELATED APPLICATIONS

This application is a continuation of U.S. patent application Ser. No. 13/706,221 filed on Dec. 5, 2012, which claims priority to U.S. Provisional Patent Application No. 61/568,618, filed Dec. 8, 2011, and which is a continuation-in-part of U.S. patent application Ser. No. 13/615,193, filed on Sep. 13, 2012, which claims priority to U.S. Provisional Patent Application No. 61/534,780, filed on Sep. 14, 2011, and which is a continuation-in-part of U.S. patent application Ser. No. 13/593,313, filed on Aug. 23, 2012, which claims priority to and the benefit of U.S. Provisional Patent Application No. 61/527,335 filed on Aug. 25, 2011 and which is a continuation-in-part of U.S. patent application Ser. No. 13/486,754, filed on Jun. 1, 2012, which issued as U.S. Pat. No. 9,149,422 on Oct. 6, 2015, which claims priority to U.S. Provisional Patent Application No. 61/493,309, filed on Jun. 3, 2011, the entire content of each of these documents being incorporated herein by this specific reference.

BACKGROUND

The present invention generally relates to dermal filler compositions, for example, but not limited to, dermal filler compositions that are effective for treatment of fine lines in skin.

Skin aging is a progressive phenomenon, occurs over time and can be affected by lifestyle factors, such as alcohol consumption, tobacco and sun exposure. Aging of the facial skin can be characterized by atrophy, slackening, and fattening. Atrophy corresponds to a massive reduction of the thickness of skin tissue. Slackening of the subcutaneous tissues leads to an excess of skin and ptosis and leads to the appearance of drooping cheeks and eye lids. Fattening refers to an increase in excess weight by swelling of the bottom of the face and neck. These changes are typically associated with dryness, loss of elasticity, and rough texture.

Hyaluronic acid (HA), also known as hyaluronan, is a non-sulfated glycosaminoglycan that is distributed widely throughout the human body in connective, epithelial, and neural tissues. Hyaluronic acid is abundant in the different layers of the skin, where it has multiple functions such as, e.g., to ensure good hydration, to assist in the organization of the extracellular matrix, to act as a filler material; and to participate in tissue repair mechanisms. However, with age, the quantity of hyaluronic acid, collagen, elastin, and other matrix polymers present in the skin decreases. For example, repeated exposed to ultra violet light, e.g., from the sun, causes dermal cells to both decrease their production of hyaluronan as well as increase the rate of its degradation. This loss of materials results in various skin conditions such as, e.g., wrinkling, hollowness, loss of moisture and other undesirable conditions that contribute to the appearance of aging Injectable dermal fillers have been successfully used in treating the aging skin. The fillers can replace lost endogenous matrix polymers, or enhance/facilitate the function of existing matrix polymers, in order to treat these skin conditions.

In humans, the residence time of un modified hyaluronic acid is a few days, as the polymer chains are easily degraded by enzymes and free radicals found in the body. Commercially available dermal fillers are generally prepared by the crosslinking of hydroxyl groups of HA a chemical crosslinker. Commercial dermal filler gels are available which contain hyaluronic acid synthesized with divinyl sulfone (DVS), 1,4-butanediol diglycidyl ether (BDDE), or 1,2,7,8-diepoxyoctane (DEO). The softness and tissue augmentation effect of dermal fillers can be controlled by changing the cross-linking density with various crosslinkers.

To improve on the residence time, the linear chains of hyaluronic acid are typically crosslinked with a small molecular crosslinker like BDDE. Crosslinking is performed at very high pH (>12) and at temperatures of about 50° C. It has been reported that the degradation rate constant of HA is increased roughly 100 times when the temperature and pH are both increased from 40 to 60° C. and 7 to 11 respectively. This drawback has led to the quest for new crosslinkers and crosslinking chemistries for HA that would involve milder conditions.

In the present invention, crosslinking HA is crosslinked with a coupling agent and the use of small multiamine crosslinkers, which form amide bonds with the carboxylic functional groups of HA chains. In the present invention, crosslinking may be done at low pH levels, for example, at a pH between 4-7 and temperatures between 20 and 37° C., conditions at which degradation of HA is minimal.

Bioconjugate Chemistry, 2010, 21, 240-247: Joem Y., et al., *Effect of cross-linking reagents for hyaluronic acid hydrogel dermal fillers on tissue augmentation and regeneration* discusses the use of HMDA to prepare a cross linked HA dermal filler for tissue augmentation. This publication is incorporated herein in its entirety by this specific reference.

Tyndall effect is an adverse event occurring in some patients administered with hyaluronic acid (HA)-based dermal fillers. Tyndall effect is characterized by the appearance of a blue discoloration at the skin site where a dermal filler had been injected, which represents visible hyaluronic acid seen through the translucent epidermis. Clinical reports suggest that filler administration technique and skin properties can influence the manifestation of this adverse event. Fillers with high stiffness and elasticity are successfully used to correct areas on the face like nasolabial folds, cheeks, and chin without any fear of facial discoloration, as the materials are injected in the mid and deep dermis regions. However, when these filler materials are used to correct superficial, fine line wrinkles, for example, tear trough, glabellar lines periorbital lines, smile lines, or forehead, or mistakenly applied too superficially in the upper regions of the dermis, a bluish discoloration of the skin is often observed. This phenomenon, which is thought to be the result of Tyndall effect, leaves a semi-permanent discoloration of the application sites, and sometimes disappears only after the administration of hyaluronidase to degrade the filler material. Consequently, Tyndall effect is more common in patients treated for superficial fine line wrinkles. Prolonged manifestation of Tyndall effect, typically for several months as long as the gel lasts in the skin, is a cause of major concern among patients.

HA-based dermal filler gels have been specifically formulated to treat "fine line" wrinkles found around the tear trough, forehead, periobital, glabellar lines, etc. Many show Tyndall effect when injected too superficially. Though these gels are formulated to have low elastic moduli by lightly crosslinking the linear HA chains with a small amount of BDDE and by reducing the final HA gel concentration, most of the commercially available fine line gels still show tyndall when injected superficially, and unfortunately, in vivo duration of these gels is quite marginal.

There is still a need for better dermal fillers for treating and improving the appearance of aging skin.

SUMMARY

The present invention describes dermal filler compositions and formulation methods for preparing HA-based dermal fillers using new crosslinking chemistries. Many of the presently described filler gels of the invention have been found to last significantly longer in vivo than current commercially available gels. In some aspects of the invention, the compositions can be administered in the upper dermis without producing any bluish discoloration of the skin, or at least no significant or noticeable bluish discoloration. In some aspects of the invention, the dermal filler compositions are optically transparent and can be used to enhance the appearance of the skin, e.g. add volume, fullness and reduce wrinkles and fine lines, without causing the blue discoloration known as "tyndalling, which is sometimes associated with conventional optically transparent dermal fillers.

In one aspect of the present invention, long lasting, therapeutic dermal filler compositions are provided which generally comprise a biocompatible polymer, for example, a hyaluronic acid component crosslinked with a di-amine or multiamine crosslinker.

In another aspect, such compositions are substantially optically transparent, and exhibit reduced or no perceptible blue discoloration when administered into a dermal region of a patient.

Methods of making an injectable dermal filler composition are also provided. In one embodiment, the method comprises the steps of crosslinking hyaluronic acid (HA) with a multiamine crosslinker with the aid of a carbodiimide coupling agent.

In one aspect, the crosslinker is made up of at least three and a most eight PEG chains emanating from a central point, each chain having a terminal amine group.

The crosslinker may contain PEG chains, for example, PEG chains having a least one ethylene glycol unit and not more than 55 ethylene glycol units.

In one aspect, the crosslinker is lysine methyl ester.

In another aspect, the crosslinker is 3-[3-(3-amino propoxy)-2,2-bis(3-amino-propoxymethyl)-propoxy]-propylamine (4 AA) and is present at a concentration between about 10 μM to about 50 μM.

In one aspect, the HA is crosslinked in conjunction with a carbodiimide coupling agent, for example, a water soluble coupling agent, for example, a water soluble carbodiimide.

In another embodiment, the coupling agent is 1-ethyl-3-[3-dimethylaminopropyl]carbodiimide hydrochloride (EDC), and is present at a concentration between about 20 μM to 100 μM.

The coupling agent may be used in conjunction with a water soluble activating agent, for example, N-hydroxysuccinimide (NHS) or N-hydroxysulfosuccinimide (sulfoNHS), present at a concentration between about 5 μM to about 25 μM.

In one embodiment, the polymer is a polysaccharide, for example, hyaluronic acid. The hyaluronic acid includes a crosslinked component and may further include a non-crosslinked component. The additive may comprise a vitamin, for example, vitamin C, for example, a stabilized form of vitamin C, or a vitamin C derivative, for example, L-ascorbic acid 2-glucoside (AA2G), ascobyl 3-aminopropyl phosphate (Vitagen) or sodium ascorbyl phosphate (AA2P).

In one aspect of the invention, the additive is a vitamin derivative which is covalently conjugated to the polymer by a suitable reaction process, for example, etherification, amidization or estherification.

The composition may be substantially optically transparent. The compositions. generally have a G' value of between about 20 Pa and about 150 Pa, for example, no greater than about 150 Pa and, for example, no less than about 20 Pa.

In another aspect of the invention, methods of treating fine lines in the skin of a patient are provided. In one embodiment, the method comprises the steps of introducing, into skin of a patient, a composition comprising a hyaluronic acid component crosslinked with a di-amine or multiamine crosslinker; and a carbodiimide coupling agent. The composition may be substantially optically transparent, and exhibits reduced or no perceptible blue discoloration when administered into a dermal region of a patient.

In another aspect of the invention, methods of improving aesthetic appearance of a face are provided, the methods generally comprising the steps of administering, to a dermal region of a patient, a substantially optically transparent dermal filler composition that exhibits no or insignificant Tyndall effect. The composition may be made by the steps of crosslinking hyaluronic acid (HA) with a di-amine or multiamine crosslinker in the presence of a carbodiimide coupling agent.

In yet another aspect of the invention, methods of reducing appearance of fine lines in thin skin regions of a patient are provided, wherein the method generally comprises administering to the patient a dermal filler composition, at a depth of no greater than about 1 mm, a substantially optically transparent hyaluronic acid based dermal filler composition comprising a hyaluronic acid component crosslinked with a di-amine or multiamine crosslinker.

In some embodiments, the composition is injected superficially, that is, at a depth of a depth of no greater than about 0.8 mm, no greater than about 0.6 mm, or no greater than about 0.4 mm.

In yet another aspect of the invention, a dermal filler composition is provided which is generally comprises a hyaluronic acid component crosslinked with a di-amine or multiamine crosslinker in the presence of a carbodiimide coupling agent. The composition may have a hyaluronic acid concentration of between about 14 mg/ml and about 30 mg/ml. The hyaluronic acid may be a low molecular weight hyaluronic acid, for example, a hyaluronic acid having a mean molecular weight of less than about 100K Da, less than 800 KDa, less than about 600 KDa, or less than about 400 KDa. These compositions may be especially useful and effective in treating folds and wrinkles, including fine lines or superficial creases in the skin, for example, even in very thin skin, for example, skin having a thickness of no greater than about 1 mm. In some embodiments, the compositions of the invention last at least 3 months, at least 6 months or up to a year after being introduced into the skin.

These and other aspects and advantages of the present invention may be more readily understood and appreciated with referenced to the following drawings and detailed description.

BRIEF DESCRIPTION OF THE DRAWINGS

FIG. 1 shows images of skin of a mammal having injected therein a composition in accordance with one aspect of the invention and two commercial dermal fillers.

FIG. 2 shows a bar chart illustrating longevity in vivo of compositions in accordance with one aspect of the invention, compared to a commercial dermal filler.

DETAILED DESCRIPTION

Hyaluronic acid (HA) is a naturally occurring glucosaminoglycan used to formulate dermal fillers that are used mainly for wrinkle reduction and volumizing of the face. In humans, the residence time of unmodified hyaluronic acid is a few days, as the polymer chains are easily degraded by enzymes and free radicals found in the body. To improve on the residence time, the linear chains of hyaluronic acid are usually crosslinked with a small molecular crosslinker like BDDE.

The present disclosure relates, in part to dermal fillers comprising crosslinked HA small di-amine and multiamine crosslinkers, which form amide bonds with the carboxylic functional groups of HA chains. In ideal conditions, EDC activates the carboxylic acid groups of HA, and the activated carboxylic acid groups then react with the amines. In one aspect, crosslinking is done at pH between about 4 and about 7 and at temperatures between about 20° C. and about 37° C. Under these conditions, it has been discovered that degradation of HA is minimal.

Linear diamine crosslinkers like hexamethylene diamine (HMDA), lysine, lysine methyl ester, have been used to crosslink HA for various applications. The problem with crosslinking HA via EDC chemistry is the concurrent formation of ester bonds between carboxylic acid groups and the hydroxyl groups of HA even in the presence of these multiamines.

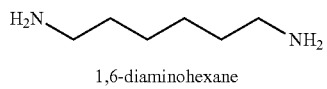

1,6-diaminohexane

Ester bonds are very labile, and are easily hydrolyzed at high temperatures. HA hydrogels made by ester crosslinking are generally not robust and cannot be sterilized with moist steam.

It has been a challenge to minimize the formation of ester bonds during EDC mediated crosslinking of HA by amines. In one approach, a high $NH_2$:HA feed ratio is used, and addition of the amine to the hydrated HA is done before addition of EDC. This seems to increase the number of amide bonds formed with respect to the number of ester bonds. It is believed that since amine groups are better nucleophiles than hydroxyl groups, more amide bonds are expected to be formed. Another approach is performing the crosslinking at high pH in order to minimize ester bond formation, as these bonds are less stable at higher pH. One other method is to use a very low HA reaction concentration, for example, at between about 1% and about 5 wt %. At such low concentrations, the HA chains are far apart, minimizing the hydroxyl and activated carboxylic groups to come into close contact for reaction to occur. The success of these methods to improve gel stability has been only marginal. Moreover, some of these methods do create other problems. For example, the efficiency of EDC is greatly reduced at high pH therefore crosslinking HA at high pH greatly reduces crosslinking structural robustness of the gel, and while crosslinking at very low HA concentration might reduce ester bond formation, it increases inefficient crosslinking of diamines, resulting in gels with too many pendent amine groups.

In accordance with one embodiment of the present invention, formulation methods are provided for the preparation of stable HA based hydrogels via EDC chemistry. Instead of using linear small molecules end capped with amino groups, a "4 Arm PEG Amine", 3-[3-(3-amino propoxy)-2,2-bis(3-amino-propoxymethyl)-propoxy]-propylamine or 4 AA (see below) is used as the crosslinker.

Unlike diamines with only two amine functionality, 4 AA has four amine functional groups which can all be used in crosslinking. Unlike with diamines where the best case scenario is for a molecule of diamine to crosslink a maximum of two HA chains, one molecule of 4 AA can crosslink a maximum of 4 HA chains. The use of 4 AA has been found to greatly enhance crosslinking efficiency, resulting in robust hydrogels that are easily sterilized by moist steam without fear of imparting structural damage to the gel.

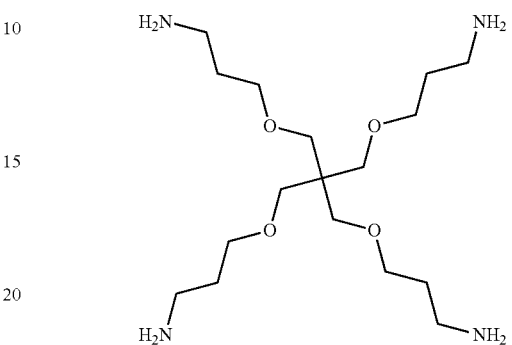

3-[3-(3-amino propoxy)-2,2-bis(3-amino-propoxymethyl)-propoxy]-propylamine, or 4 AA Also provided herein are methods for preparing HA hydrogels crosslinked with HMDA and methods of preparing HA-lysine hydrogels using lysine methyl ester as the crosslinker. These gels are biocompatible and can easily be extruded through a syringe and needle for minimal invasive implantation.

In one aspect of the invention, dermal filler compositions are provided for decreasing the appearance of fine lines or superficial wrinkles in the face.

The compositions generally comprising a biocompatible polymer, for example, a polysaccharide such as a hyaluronic acid, crosslinked with a di-amine or multiamine crosslinker. The composition is substantially optically transparent and exhibits reduced or no perceptible blue discoloration when administered into a dermal region of a patient.

The polymer may be selected from the group of polymers consisting of proteins, peptides and polypeptides, polylysine, collagens, pro-collagens, elastins, and laminins.

The polymer may be selected from the group of polymers consisting of synthetic polymers with hydroxyl, amine, and carboxyl functional groups: poly(vinyl alcohol), polyethylene glycol, polyvinyl amine, polyallylamine, deacetylated polyacrylamide, polyacrylic acid, and polymethacrylic acid. The polymer may be selected from the group of polymers consisting of dentric or branched polymers, including dentric polyols and dentric polyamines. The polymer may be selected from the group of polymers consisting of solid surface with hydroxyl, amine, and carboxyl functional groups.

The polymer may be a polysaccharide, for example, selected from the group of polysaccharides including starch and its derivatives; dextran and its derivatives, cellulose and its derivatives; chitin and chitosan and alginate and its derivatives.

In an exemplary embodiment of the invention, the polymer is glycosaminoglycan. The hydrogel composition disclosed herein can further comprise two or more different glycosaminoglycan polymers. As used herein, the term "glycosaminoglycan" is synonymous with "GAG" and "mucopolysaccharide" and refers to long unbranched polysaccharides consisting of a repeating disaccharide units. The repeating unit consists of a hexose (six-carbon sugar) or a hexuronic acid, linked to a hexosamine (six-carbon sugar containing nitrogen) and pharmaceutically acceptable salts thereof. Members of the GAG family vary in the type of hexosamine, hexose or hexuronic acid unit they contain, such as, e.g., glucuronic acid, iduronic acid, galactose, galactosamine, glucosamine) and may also vary in the geometry of the glycosidic linkage. Any glycosaminoglycan polymer is useful in the hydrogel compositions disclosed herein with the proviso that the glycosaminoglycan polymer improves a condition of the skin. Non-limiting examples of and Hydrogels thus Obtained, U.S. Patent Publication 2006/0194758; and Di Napoli, Composition and Method for Intradermal Soft Tissue Augmentation, International Patent Publication WO 2004/073759, each of which is hereby incorporated by reference in its entirety. GAGs useful in the hydrogel compositions and methods disclosed herein are commercially available, such as, e.g., hyaluronan-based dermal fillers JUVEDERM®, JUVEDERM® 30, JUVEDERM® Ultra, JUVEDERM® Ultra Plus, JUVEDERM® Ultra XC, and JUVEDERM® Ultra Plus XC (Allergan Inc, Irvine, Calif.). Table 1 lists representative GAGs.

TABLE 1

Examples of GAGs

| Name | Hexuronic acid/Hexose | Hexosamine | Glycosidic linkage geometry | Unique features |
|---|---|---|---|---|
| Chondroitin sulfate | GlcUA or GlcUA(2S) | GalNAc or GalNAc(4S) or GalNAc(6S) or GalNAc(4S,6S) | -4GlcUA$\beta$1-3GalNAc$\beta$1- | Most prevalent GAG |
| Dermatan sulfate | GlcUA or IdoUA or IdoUA(2S) | GalNAc or GalNAc(4S) or GalNAc(6S) or GalNAc(4S,6S) | -4IdoUA$\beta$1-3GalNAc$\beta$1- | Distinguished from chondroitin sulfate by the presence of iduronic acid, although some hexuronic acid monosaccharides may be glucuronic acid. |
| Keratan sulfate | Gal or Gal(6S) | GlcNAc or GlcNAc(6S) | -3Gal(6S)$\beta$1-4GlcNAc(6S)$\beta$1- | Keratan sulfate type II may be fucosylated. |
| Heparin | GlcUA or IdoUA(2S) | GlcNAc or GlcNS or GlcNAc(6S) or GlcNS(6S) | -4IdoUA(2S)$\alpha$1-4GlcNS(6S)$\alpha$1- | Highest negative charge density of any known biological molecule |
| Heparan sulfate | GlcUA or IdoUA or IdoUA(2S) | GlcNAc or GlcNS or GlcNAc(6S) or GlcNS(6S) | -4GlcUA$\beta$1-4GlcNAc$\alpha$1- | Highly similar in structure to heparin, however heparan sulfates disaccharide units are organized into distinct sulfated and non-sulfated domains. |
| Hyaluronan | GlcUA | GlcNAc | -4GlcUA$\beta$1-3GlcNAc$\beta$1- | The only GAG that is exclusively non-sulfated |

GlcUA = $\beta$-D-glucuronic acid
GlcUA(2S) = 2-O-sulfo-$\beta$-D-glucuronic acid
IdoUA = $\alpha$-L-iduronic acid
IdoUA(2S) = 2-O-sulfo-$\alpha$-L-iduronic acid
Gal = $\beta$-D-galactose
Gal(6S) = 6-O-sulfo-$\beta$-D-galactose
GalNAc = $\beta$-D-N-acetylgalactosamine
GalNAc(4S) = $\beta$-D-N-acetylgalactosamine-4-O-sulfate
GalNAc(6S) = $\beta$-D-N-acetylgalactosamine-6-O-sulfate
GalNAc(4S,6S) = $\beta$-D-N-acetylgalactosamine-4-O, 6-O-sulfate
GlcNAc = $\alpha$-D-N-acetylglucosamine
GlcNS = $\alpha$-D-N-sulfoglucosamine
GlcNS(6S) = $\alpha$-D-N-sulfoglucosamine-6-O-sulfate glycosaminoglycans include chondroitin sulfate, dermatan sulfate, keratan sulfate, hyaluronan. Non-limiting examples of an acceptable salt of a glycosaminoglycans includes sodium salts, potassium salts, magnesium salts, calcium salts, and combinations thereof. Glycosaminoglycan and their resulting polymers useful in the hydrogel compositions and methods disclosed herein are described in, e.g., Piron and Tholin, Polysaccharide Crosslinking, Hydrogel Preparation, Resulting Polysaccharides(s) and Hydrogel(s), uses Thereof, U.S. Patent Publication 2003/0148995; Lebreton, Cross-Linking of Low and High Molecular Weight Polysaccharides Preparation of Injectable Monophase Hydrogels; Lebreton, Viscoelastic Solutions Containing Sodium Hyaluronate and Hydroxypropyl Methyl Cellulose, Preparation and Uses, U.S. Patent Publication 2008/0089918; Lebreton, Hyaluronic Acid-Based Gels Including Lidocaine, U.S. Patent Publication 2010/0028438; and Polysaccharides Aspects of the present specification provide, in part, a hydrogel composition comprising a hyaluronan polymer. As used herein, the term "hyaluronic acid polymer" is synonymous with "HA polymer", "hyaluronic acid polymer", and "hyaluronate polymer" refers to an anionic, non-sulfated glycosaminoglycan polymer comprising disaccharide units, which themselves include D-glucuronic acid and D-N-acetylglucosamine monomers, linked together via alternating $\beta$-1,4 and $\beta$-1,3 glycosidic bonds and pharmaceutically acceptable salts thereof. Hyaluronan polymers can be purified from animal and non-animal sources. Polymers of hyaluronan can range in size from about 5,000 Da to about 20,000,000 Da. Any hyaluronan polymer is useful in the compositions disclosed herein with the proviso that the hyaluronan improves a condition of the skin. Non-limiting examples of pharmaceutically acceptable salts of hyaluronan include sodium hyaluronan, potassium hyaluronan, magnesium hyaluronan, calcium hyaluronan, and combinations thereof.

Aspects of the present specification provide, in part, a hydrogel composition comprising a crosslinked glycosaminoglycan polymer. As used herein, the term "crosslinked" refers to the intermolecular bonds joining the individual polymer molecules, or monomer chains, into a more stable structure like a gel. As such, a crosslinked glycosaminoglycan polymer has at least one intermolecular bond joining at least one individual polymer molecule to another one. The crosslinking of glycosaminoglycan polymers typically result in the formation of a hydrogel. Such hydrogels have high viscosity and require considerable force to extrude through a fine needle.

Glycosaminoglycan polymers disclosed herein may be crosslinked using dialdehydes and disufides crosslinking agents including, without limitation, multifunctional PEG-based crosslinking agents, divinyl sulfones, diglycidyl ethers, and bis-epoxides, biscarbodiimide. Non-limiting examples of hyaluronan crosslinking agents include multifunctional PEG-based crosslinking agents like pentaerythritol tetraglycidyl ether (PETGE), divinyl sulfone (DVS), 1,4-butanediol diglycidyl ether (BDDE), 1,2-bis(2,3-epoxypropoxy)ethylene (EGDGE), 1,2,7,8-diepoxyoctane (DEO), (phenylenebis-(ethyl)-carbodiimide and 1,6 hexamethylenebis(ethylcarbodiimide), adipic dihydrazide (ADH), bis(sulfosuccinimidyl)suberate (BS), hexamethylenediamine (NMDA), 1-(2,3-epoxypropyl)-2,3-epoxycyclohexane, lysine, lysine methyl ester, or combinations thereof.

In other aspects of the invention, the crosslinker is a di-amine or multiamine crosslinker. In another aspect, the crosslinker is made up of at least three and a most eight PEG chains emanating from a central point, each chain having a terminal amine group. The crosslinker may contain PEG chains having a least one ethylene glycol unit and not more than 55 ethylene glycol units.

Other useful cross-linking agents are disclosed in Stroumpoulis and Tezel, Tunably Crosslinked Polysaccharide Compositions, U.S. patent application Ser. No. 12/910,466, filed Oct. 22, 2010, which is incorporated by reference in its entirety. Non-limiting examples of methods of crosslinking glycosaminoglycan polymers are described in, e.g., Glycosaminoglycan polymers useful in the compositions and methods disclosed herein are described in, e.g., Piron and Tholin, Polysaccharide Crosslinking, Hydrogel Preparation, Resulting Polysaccharides(s) and Hydrogel(s), uses Thereof, U.S. Patent Publication 2003/0148995; Lebreton, Cross-Linking of Low and High Molecular Weight Polysaccharides Preparation of Injectable Monophase Hydrogels; Lebreton, Viscoelastic Solutions Containing Sodium Hyaluronate and Hydroxypropyl Methyl Cellulose, Preparation and Uses, U.S. Patent Publication 2008/0089918; Lebreton, Hyaluronic Acid-Based Gels Including Lidocaine, U.S. Patent Publication 2010/0028438; and Polysaccharides and Hydrogels thus Obtained, U.S. Patent Publication 2006/0194758; and Di Napoli, Composition and Method for Intradermal Soft Tissue Augmentation, International Patent Publication WO 2004/073759, each of which is hereby incorporated by reference in its entirety.

Aspects of the present specification provide, in part, a hydrogel composition comprising a crosslinked glycosaminoglycan polymer having a degree of crosslinking. As used herein, the term "degree of crosslinking" refers to the percentage of glycosaminoglycan polymer monomeric units, such as, e.g., the disaccharide monomer units of hyaluronan that are bound to a cross-linking agent. The degree of crosslinking is expressed as the percent weight ratio of the crosslinking agent to glycosaminoglycan. The degree of crosslinking in certain advantageous embodiment of the invention is between about 3% and about 12%, for example, between about 5% and about 10%. The crosslinker is present in the composition at a concentration between about 1 µM to about 100 µM, for example, between about 10 µM to about 50 µM.

In an embodiment, a hydrogel composition comprises a crosslinked glycosaminoglycan polymer, for example, crosslinked hyaluronic acid, wherein the crosslinked glycosaminoglycan polymer is present in the composition at a concentration of, for example, between about 10 mg/ml and about 40 mg/ml, for example, between about 18 mg/ml and about 30 mg/ml. In some embodiments, the compositions have a total hyaluronic acid concentration of about 22 mg/ml, about 23 mg/ml, about 24 mg/ml or about 25 mg/ml.

Aspects of the present specification provide, in part, a hydrogel composition comprising hyaluronan polymers of low molecular weight, hyaluronan polymers of high molecular weight, or hyaluronan polymers of both low and high molecular weight.

As used herein, the term "high molecular weight" when referring to "hyaluronan" refers to hyaluronan polymers having a mean molecular weight of 1,000,000 Da or greater. Non-limiting examples of a high molecular weight hyaluronan polymers include hyaluronan polymers about 1,500,000 Da, about 2,000,000 Da, about 2,500,000 Da, about 3,000,000 Da, about 3,500,000 Da, about 4,000,000 Da, about 4,500,000 Da, and about 5,000,000 Da. As used herein, the term "low molecular weight" when referring to "hyaluronan" refers to hyaluronan polymers having a mean molecular weight of less than 1,000,000 Da. Non-limiting examples of a low molecular weight hyaluronan polymers include hyaluronan polymers of about 200,000 Da, about 300,000 Da, about 400,000 Da, about 500,000 Da, about 600,000 Da, about 700,000 Da, of about 800,000 Da, and about 900,000 Da.

In an embodiment, a composition comprises crosslinked hyaluronan polymers of low molecular weight. In aspects of this embodiment, a composition comprises crosslinked hyaluronan polymers having a mean molecular weight of, e.g., about 100,000 Da, about 200,000 Da, about 300,000 Da, about 400,000 Da, about 500,000 Da, about 600,000 Da, about 700,000 Da, about 800,000 Da, or about 900,000 Da. In yet other aspects of this embodiment, a composition comprises crosslinked hyaluronan polymers having a mean molecular weight of, e.g., at most 100,000 Da, at most 200,000 Da, at most 300,000 Da, at most 400,000 Da, at most 500,000 Da, at most 600,000 Da, at most 700,000 Da, at most 800,000 Da, at most 900,000 Da, or at most 950,000 Da. In still other aspects of this embodiment, a composition comprises crosslinked hyaluronan polymers having a mean molecular weight of, e.g., about 100,000 Da to about 500,000 Da, about 200,000 Da to about 500,000 Da, about 300,000 Da to about 500,000 Da, about 400,000 Da to about 500,000 Da, about 500,000 Da to about 950,000 Da, about 600,000 Da to about 950,000 Da, about 700,000 Da to about 950,000 Da, about 800,000 Da to about 950,000 Da, about 300,000 Da to about 600,000 Da, about 300,000 Da to about 700,000 Da, about 300,000 Da to about 800,000 Da, or about 400,000 Da to about 700,000 Da.

In another embodiment, a composition comprises crosslinked hyaluronan polymers of high molecular weight. In aspects of this embodiment, a composition comprises a crosslinked hyaluronan polymers having a mean molecular weight of, e.g., about 1,000,000 Da, about 1,500,000 Da, about 2,000,000 Da, about 2,500,000 Da, about 3,000,000 Da, about 3,500,000 Da, about 4,000,000 Da, about 4,500,000 Da, or about 5,000,000 Da. In yet other aspects of this embodiment, a composition comprises a crosslinked hyaluronan polymers having a mean molecular weight of, e.g., at least 1,000,000 Da, at least 1,500,000 Da, at least 2,000,000 Da, at least 2,500,000 Da, at least 3,000,000 Da, at least 3,500,000 Da, at least 4,000,000 Da, at least 4,500,000 Da, or at least 5,000,000 Da. In still other aspects of this embodiment, a composition comprises a crosslinked hyaluronan polymers having a mean molecular weight of, e.g., about 1,000,000 Da to about 5,000,000 Da, about 1,500,000 Da to about 5,000,000 Da, about 2,000,000 Da to about 5,000,000 Da, about 2,500,000 Da to about 5,000,000 Da, about 2,000,000 Da to about 3,000,000 Da, about 2,500,000 Da to about 3,000,000 Da.

In yet another embodiment, a composition comprises a crosslinked hyaluronan polymers where the crosslinked hyaluronan polymers comprise a combination of both high molecular weight hyaluronan polymers and low molecular weight hyaluronan polymers, in various ratios. In aspects of this embodiment, a composition comprises a crosslinked hyaluronan polymers where the crosslinked hyaluronan polymers comprises a combination of both high molecular weight hyaluronan polymers and low molecular weight hyaluronan polymers in a ratio of about 20:1, about 15:1, about 10:1, about 5:1, about 1:1, about 1:5 about 1:10, about 1:15, or about 1:20.

Aspects of the present specification provide, in part, a hydrogel composition comprising an uncrosslinked glycosaminoglycan polymer. As used herein, the term "uncrosslinked" refers to a lack of intermolecular bonds joining the individual glycosaminoglycan polymer molecules, or monomer chains. As such, an uncrosslinked glycosaminoglycan polymer is not linked to any other glycosaminoglycan polymer by an intermolecular bond. In aspects of this embodiment, a composition comprises an uncrosslinked chondroitin sulfate polymer, an uncrosslinked dermatan sulfate polymer, an uncrosslinked keratan sulfate polymer, an uncrosslinked heparan polymer, an uncrosslinked heparan sulfate polymer, or an uncrosslinked hyaluronan polymer. Uncrosslinked glycosaminoglycan polymers are water soluble and generally remain fluid in nature. As such, uncross-linked glycosaminoglycan polymers are often mixed with a glycosaminoglycan polymer-based hydrogel composition as a lubricant to facilitate the extrusion process of the composition through a fine needle.

In an embodiment, a composition comprises an uncrosslinked glycosaminoglycan polymer where the uncrosslinked glycosaminoglycan polymer is present at a concentration of, e.g., about 2 mg/g, about 3 mg/g, about 4 mg/g, about 5 mg/g, about 6 mg/g, about 7 mg/g, about 8 mg/g, about 9 mg/g, about 10 mg/g, about 11 mg/g, about 12 mg/g, about 13 mg/g, about 13.5 mg/g, about 14 mg/g, about 15 mg/g, about 16 mg/g, about 17 mg/g, about 18 mg/g, about 19 mg/g, about 20 mg/g, about 40 mg/g, or about 60 mg/g. In other aspects of this embodiment, a composition comprises an uncrosslinked glycosaminoglycan where the uncrosslinked glycosaminoglycan is present at a concentration of, e.g., at least 1 mg/g, at least 2 mg/g, at least 3 mg/g, at least 4 mg/g, at least 5 mg/g, at least 10 mg/g, at least 15 mg/g, at least 20 mg/g, at least 25 mg/g at least 35 mg/g, or at least 40 mg/g. In yet other aspects of this embodiment, a composition comprises an uncrosslinked glycosaminoglycan where the uncrosslinked glycosaminoglycan is present at a concentration of, e.g., at most 1 mg/g, at most 2 mg/g, at most 3 mg/g, at most 4 mg/g, at most 5 mg/g, at most 10 mg/g, at most 15 mg/g, at most 20 mg/g, or at most 25 mg/g. In still other aspects of this embodiment, a composition comprises an uncrosslinked glycosaminoglycan where the uncrosslinked glycosaminoglycan is present at a concentration of, e.g., about 1 mg/g to about 60 mg/g, about 10 mg/g to about 40 mg/g, about 7.5 mg/g to about 19.5 mg/g, about 8.5 mg/g to about 18.5 mg/g, about 9.5 mg/g to about 17.5 mg/g, about 10.5 mg/g to about 16.5 mg/g, about 11.5 mg/g to about 15.5 mg/g, or about 12.5 mg/g to about 14.5 mg/g.

Aspects of the present specification provide, in part, a hydrogel composition comprising a ratio of crosslinked glycosaminoglycan polymer and uncrosslinked glycosaminoglycan polymer. This ratio of crosslinked and uncrosslinked glycosaminoglycan polymer is also known as the gel:fluid ratio. Any gel:fluid ratio is useful in making the compositions disclosed herein with the proviso that such ratio produces a composition disclosed herein that improves a skin condition as disclosed herein. Non-limiting examples of gel:fluid ratios in compositions of the present invention include 100:0, 98:2, 90:10, 75:25, 70:30, 60:40, 50:50, 40:60, 30:70, 25:75, 10:90; 2:98, and 0:100.

In aspects of this embodiment, a composition comprises a crosslinked glycosaminoglycan polymer and an uncrosslinked glycosaminoglycan polymer where the gel:fluid ratio is, e.g., about 0:100, about 1:99, about 2:98, about 3:97, about 4:96, about 5:95, about 6:94, about 7:93, about 8:92, about 9:91, or about 10:90. In other aspects of this embodiment, a composition comprises a crosslinked glycosaminoglycan polymer and an uncrosslinked glycosaminoglycan polymer where the gel:fluid ratio is, e.g., at most 1:99, at most 2:98, at most 3:97, at most 4:96, at most 5:95, at most 6:94, at most 7:93, at most 8:92, at most 9:91, or at most 10:90. In yet other aspects of this embodiment, a composition comprises a crosslinked glycosaminoglycan polymer and an uncrosslinked glycosaminoglycan polymer where the gel:fluid ratio is, e.g., about 0:100 to about 3:97, about 0:100 to about 5:95, or about 0:100 to about 10:90.

A hydrogel composition disclosed herein may further comprise another agent or combination of agents that provide a beneficial effect when the composition is administered to an individual. Such beneficial agents include, without limitation, an antioxidant, an anti-itch agent, an anti-cellulite agent, an anti-scarring agent, an anti-inflammatory agent, an anesthetic agent, an anti-irritant agent, a vasoconstrictor, a vasodilator, an anti-hemorrhagic agent like a hemostatic agent or anti-fibrinolytic agent, a desquamating agent, a tensioning agent, an anti-acne agent, a pigmentation agent, an anti-pigmentation agent, or a moisturizing agent.

For purposes of the present specification, unless otherwise stated, "%" in a formulation is defined as weight by weight (i.e., w/w) percentage.

Aspects of the present specification provide, in part, a hydrogel composition disclosed herein that may comprise a coupling agent. The coupling agent may be a water soluble coupling agent, for example, a water soluble carbodiimide. In one embodiment, the coupling agent is 1-ethyl-3-[3-dimethylaminopropyl]carbodiimide hydrochloride (EDC). The concentration of the coupling agent may be between about 10 µM to about 50 µM Aspects of the present specification provide, in part, that a coupling agent may be used in conjunction with a water soluble activating agent. The activating agent may be N-hydroxysuccinimide (NHS) or N-hydroxysulfosuccinimide (sulfoNHS). The activating agent is present at a concentration between about 5 µM to about 25 µM.

Aspects of the present specification provide, in part, a hydrogel composition disclosed herein that may optionally comprise an anesthetic agent. An anesthetic agent is preferably a local anesthetic agent, i.e., an anesthetic agent that causes a reversible local anesthesia and a loss of nociception, such as, e.g., aminoamide local anesthetics and aminoester local anesthetics. The amount of an anesthetic agent included in a composition disclosed herein is an amount effective to mitigate pain experienced by an individual upon administration of the composition. As such, the amount of an anesthetic agent included in a composition disclosed in the present specification is between about 0.1% to about 5% by weight of the total composition. Non-limiting examples of anesthetic agents include lidocaine, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquin, dimethocaine, diperodon, dycyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, psuedococaine, pyrrocaine, ropivacaine, salicyl alcohol, tetracaine, tolycaine, trimecaine, zolamine, combinations thereof, and salts thereof. Non-limiting examples of aminoester local anesthetics include procaine, chloroprocaine, cocaine, cyclomethycaine, cimethocaine (larocaine), propoxycaine, procaine (novocaine), proparacaine, tetracaine (amethocaine). Non-limiting examples of aminoamide local anesthetics include articaine, bupivacaine, cinchocaine (dibucaine), etidocaine, levobupivacaine, lidocaine (lignocaine), mepivacaine, piperocaine, prilocaine, ropivacaine, and trimecaine. A composition disclosed herein may comprise a single anesthetic agent or a plurality of anesthetic agents. A non-limiting example of a combination local anesthetic is lidocaine/prilocaine (EMLA).

Thus in an embodiment, a composition disclosed herein comprises an anesthetic agent and salts thereof. In aspects of this embodiment, a composition disclosed herein comprises an aminoamide local anesthetic and salts thereof or an aminoester local anesthetic and salts thereof. In other aspects of this embodiment, a composition disclosed herein comprises procaine, chloroprocaine, cocaine, cyclomethycaine, cimethocaine, propoxycaine, procaine, proparacaine, tetracaine, or salts thereof, or any combination thereof. In yet other aspects of this embodiment, a composition disclosed herein comprises articaine, bupivacaine, cinchocaine, etidocaine, levobupivacaine, lidocaine, mepivacaine, piperocaine, prilocaine, ropivacaine, trimecaine, or salts thereof, or any combination thereof. In still other aspects of this embodiment, a composition disclosed herein comprises a lidocaine/prilocaine combination.

In other aspects of this embodiment, a composition disclosed herein comprises an anesthetic agent in an amount of, e.g., about 0.1%, about 0.2%, about 0.3%, about 0.4%, about 0.5%, about 0.6%, about 0.7%, about 0.8% about 0.9%, about 1.0%, about 2.0%, about 3.0%, about 4.0%, about 5.0%, about 6.0%, about 7.0%, about 8.0%, about 9.0%, or about 10% by weight of the total composition. In yet other aspects, a composition disclosed herein comprises an anesthetic agent in an amount of, e.g., at least 0.1%, at least 0.2%, at least 0.3%, at least 0.4%, at least 0.5%, at least 0.6%, at least 0.7%, at least 0.8% at least 0.9%, at least 1.0%, at least 2.0%, at least 3.0%, at least 4.0%, at least 5.0%, at least 6.0%, at least 7.0%, at least 8.0%, at least 9.0%, or at least 10% by weight of the total composition. In still other aspects, a composition disclosed herein comprises an anesthetic agent in an amount of, e.g., at most 0.1%, at most 0.2%, at most 0.3%, at most 0.4%, at most 0.5%, at most 0.6%, at most 0.7%, at most 0.8% at most 0.9%, at most 1.0%, at most 2.0%, at most 3.0%, at most 4.0%, at most 5.0%, at most 6.0%, at most 7.0%, at most 8.0%, at most 9.0%, or at most 10% by weight of the total composition. In further aspects, a composition disclosed herein comprises an anesthetic agent in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.2% to about 0.9%, about 0.2% to about 1.0%, about 0.2% to about 2.0%, about 0.5% to about 1.0%, or about 0.5% to about 2.0% by weight of the total composition.

In one aspect of the present invention, an injectable dermal filler is provided which comprises a polymer, for example, a glycosaminoglycan polymer, for example a hyaluronic acid polymer, for example, a hyaluronic acid at least a portion of which is crosslinked, and an additive or beneficial agent combined with the polymer.

Aspects of the present specification provide, in part, a hydrogel composition disclosed herein that exhibits an elastic modulus or storage modulus. The compositions as disclosed herein are viscoelastic in that the composition has an elastic component (solid-like such as, e.g., crosslinked glycosaminoglycan polymers) and a viscous component (liquid-like such as, e.g., uncrosslinked glycosaminoglycan polymers or a carrier phase) when a force is applied (stress, deformation).

Elastic modulus, or modulus of elasticity, refers to the ability of a hydrogel material to resists deformation, or, conversely, an object's tendency to be non-permanently deformed when a force is applied to it. Elastic modulus characterizes the firmness of a composition and is also known as the storage modulus because it describes the storage of energy from the motion of the composition. The elastic modulus describes the interaction between elasticity and strength ($G'$=stress/strain) and, as such, provides a quantitative measurement of a composition's hardness or softness. The elastic modulus of an object is defined as the slope of its stress-strain curve in the elastic deformation region: $A$=stress/strain, where $A$ is the elastic modulus in Pascal's; stress is the force causing the deformation divided by the area to which the force is applied; and strain is the ratio of the change caused by the stress to the original state of the object. Although depending on the speed at which the force is applied, a stiffer composition will have a higher elastic modulus and it will take a greater force to deform the material a given distance, such as, e.g., an injection. Specifying how stresses are to be measured, including directions, allows for many types of elastic moduli to be defined. The three primary elastic moduli are tensile modulus, shear modulus, and bulk modulus.

In aspects of this embodiment, a hydrogel composition exhibits an elastic modulus of, e.g., at least about 20 Pa to about 3000 Pa. For example the composition exhibits an elastic modulus of between, at least about 50 Pa to about 2500 Pa, at least about 100 Pa to about 2000 Pa, at least about 500 Pa to about 1000 Pa. In other aspects of this embodiment, a hydrogel composition exhibits an elastic modulus of, e.g., at least about 20 Pa, at least about 25 Pa, at least about 50 Pa, at least about 75 Pa, at least about 100 Pa, at least about 125 Pa, at least about 150 Pa, at least about 175 Pa, at least about 200 Pa, at least about 250 Pa, at least about 300 Pa, at least about 350 Pa, at least about 400 Pa, at least about 450 Pa, at least about 500 Pa, at least about 550 Pa, at least about 600 Pa, at least about 650 Pa, at least about 700 Pa, at least about 750 Pa, at least about 800 Pa, at least about 850 Pa, at least about 900 Pa, at least about 950 Pa, at least about 1,000 Pa, at least about 1,200 Pa, at least about 1,300 Pa, at least about 1,400 Pa, at least about 1,500 Pa, at least 1 about, 600 Pa, at least 1 about 700 Pa, at least about 1800 Pa, at least about 1900 Pa, at least about 2,000 Pa, at least about 2,100 Pa, at least about 2,200 Pa, at least about 2,300 Pa, at least about 2,400 Pa, or at least about 2,500 Pa. In yet other aspects of this embodiment, a hydrogel composition exhibits an elastic modulus of, e.g., at least about 20 Pa to at most about 3000 Pa.

Aspects of the present specification provide, in part, a hydrogel composition disclosed herein having a transparency and/or translucency. Optical transparency is the physical property of allowing visible light to pass through a material, whereas translucency (also called translucence or translucidity) only allows light to pass through diffusely. The opposite property is opacity. Transparent materials are clear, while translucent ones cannot be seen through clearly. The hydrogels disclosed herein may be optically transparent or at least translucent.

In an embodiment, a hydrogel composition disclosed herein is optically translucent. In aspects of this embodiment, a hydrogel composition diffusely transmits, e.g., about 75% of the light, about 80% of the light, about 85% of the light, about 90% of the light, about 95% of the light, or about 100% of the light. In other aspects of this embodiment, a hydrogel composition diffusely transmits, e.g., at least 75% of the light, at least 80% of the light, at least 85% of the light, at least 90% of the light, or at least 95% of the light. In yet other aspects of this embodiment, a hydrogel composition diffusely transmits, e.g., about 75% to about 100% of the light, about 80% to about 100% of the light, about 85% to about 100% of the light, about 90% to about 100% of the light, or about 95% to about 100% of the light. In an embodiment, a hydrogel composition disclosed herein is optically transparent and transmits 100% of visible light.

A hydrogel composition disclosed herein may be further processed by pulverizing the hydrogel into particles and optionally mixed with a carrier phase such as, e.g., water or a saline solution to form an injectable or topical substance like a solution, oil, lotion, gel, ointment, cream, slurry, salve, or paste. As such, the disclosed hydrogel compositions may be monophasic or multiphasic compositions. A hydrogel may be milled to a particle size from about 10 µm to about 1000 µm in diameter, such as about 15 µm to about 30 µm, about 50 µm to about 75 µm, about 100 µm to about 150 µm, about 200 µm to about 300 µm, about 450 µm to about 550 µm, about 600 µm to about 700 µm, about 750 µm to about 850 µm, or about 900 µm to about 1,000 µm.

Aspects of the present specification provide, in part, a composition disclosed herein is injectable. As used herein, the term "injectable" refers to a material having the properties necessary to administer the composition into a skin region of an individual using an injection device with a fine needle. As used herein, the term "fine needle" refers to a needle that is 27 gauge or smaller. Injectability of a composition disclosed herein can be accomplished by sizing the hydrogel particles as discussed above.

In aspect of this embodiment, a hydrogel composition disclosed herein is injectable through a fine needle. In other aspects of this embodiment, a hydrogel composition disclosed herein is injectable through a needle of, e.g., about 27 gauge, about 30 gauge, or about 32 gauge. In yet other aspects of this embodiment, a hydrogel composition disclosed herein is injectable through a needle of, e.g., 22 gauge or smaller, 27 gauge or smaller, 30 gauge or smaller, or 32 gauge or smaller. In still other aspects of this embodiment, a hydrogel composition disclosed herein is injectable through a needle of, e.g., about 22 gauge to about 35 gauge, 22 gauge to about 34 gauge, 22 gauge to about 33 gauge, 22 gauge to about 32 gauge, about 22 gauge to about 27 gauge, or about 27 gauge to about 32 gauge.

In aspects of this embodiment, a hydrogel composition disclosed herein can be injected with an extrusion force of about 150 N, about 100 N, about 80 N, about 60 N, about 55 N, about 50 N, about 45 N, about 40 N, about 35 N, about 30 N, about 25 N, about 20 N, or about 15 N at speeds of 100 mm/min. In other aspects of this embodiment, a hydrogel composition disclosed herein can be injected through a 27 gauge needle with an extrusion force of about 150 N or less, about 100 N or less, about 80 N or less, about 60 N or less, about 55 N or less, about 50 N or less, about 45 N or less, about 40 N or less, about 35 N or less, about 30 N or less, about 25 N or less, about 20 N or less, about 15 N or less, about 10 N or less, or about 5 N or less. In yet other aspects of this embodiment, a hydrogel composition disclosed herein can be injected through a 30 gauge needle with an extrusion force of about 150 N or less, about 100 N or less, about 80 N or less, about 60 N or less, about 55 N or less, about 50 N or less, about 45 N or less, about 40 N or less, about 35 N or less, about 30 N or less, about 25 N or less, about 20 N or less, about 15 N or less, about 10 N or less, or about 5 N or less. In still other aspects of this embodiment, a hydrogel composition disclosed herein can be injected through a 32 gauge needle with an extrusion force of about 150 N or less, about 100 N or less, about 80 N or less, about 60 N or less, about 55 N or less, about 50 N or less, about 45 N or less, about 40 N or less, about 35 N or less, about 30 N or less, about 25 N or less, about 20 N or less, about 15 N or less, about 10 N or less, or about 5 N or less.

Aspects of the present specification provide, in part, a hydrogel composition disclosed herein that exhibits cohesivity. Cohesivity, also referred to as cohesion cohesive attraction, cohesive force, or compression force is a physical property of a material, caused by the intermolecular attraction between like-molecules within the material that acts to unite the molecules. Cohesivity is expressed in terms of grams-force (gmf). Cohesiveness is affected by, among other factors, the molecular weight ratio of the initial free glycosaminoglycan polymer, the degree of crosslinking of glycosaminoglycan polymers, the amount of residual free glycosaminoglycan polymers following crosslinking, and the pH of the hydrogel composition. A composition should be sufficiently cohesive as to remain localized to a site of administration. Additionally, in certain applications, a sufficient cohesiveness is important for a composition to retain its shape, and thus functionality, in the event of mechanical load cycling. As such, in one embodiment, a hydrogel composition disclosed herein exhibits cohesivity, on par with water. In yet another embodiment, a hydrogel composition disclosed herein exhibits sufficient cohesivity to remain localized to a site of administration. In still another embodiment, a hydrogel composition disclosed herein exhibits sufficient cohesivity to retain its shape. In a further embodiment, a hydrogel composition disclosed herein exhibits sufficient cohesivity to retain its shape and functionality.

Aspects of the present specification provide, in part, a hydrogel composition disclosed herein that exhibits substantial stability. As used herein, the term "stability" or "stable" when referring to a hydrogel composition disclosed herein refers to a composition that is not prone to degrading, decomposing, or breaking down to any substantial or significant degree while stored before administration to an individual. As used herein, the term "substantial heat stability", "substantially heat stable", "autoclave stable", or "steam sterilization stable" refers to a hydrogel composition disclosed herein that is substantially stable when subjected to a heat treatment as disclosed herein.

Stability of a hydrogel composition disclosed herein can be determined by subjecting a hydrogel composition to a heat treatment, such as, e.g., steam sterilization at normal pressure or under pressure (e.g., autoclaving). The heat treatment may be carried out at a temperature of at least about 100° C. for between about one minute and about 10 minutes. Substantial stability of a hydrogel composition disclosed herein can be evaluated 1) by determining the change in the extrusion force (EF) of a hydrogel composition disclosed herein after sterilization, where the change in extrusion force less 2N is indicative of a substantially stable hydrogel composition as measured by (the extrusion force of a hydrogel composition with the specified additives) minus (the extrusion force of the a hydrogel composition without the added additives); and/or 2) by determining the change in rheological properties of a hydrogel composition disclosed herein after sterilization, where the change in tan δ 1 Hz of less than 0.1 is indicative of a substantially stable hydrogel composition as measured by (tan δ 1 Hz of gel formulation with additives) minus (tan δ 1 Hz of gel formulation without additives). As such, a substantially stable hydrogel composition disclosed herein retains one or more of the following characteristics after sterilization: homogeneousness, extrusion force, cohesiveness, hyaluronan concentration, agent(s) concentration, osmolarity, pH, or other rheological characteristics desired by the hydrogel before the heat treatment. In one embodiment, the composition is substantially stable after being sterilized with moist steam at temperatures between about 121° C. to about 124° C. or higher, for about 3 min. to about 15 min or more.

In an embodiment, a hydrogel composition comprising a glycosaminoglycan polymer is processed using a heat treatment that maintains the desired hydrogel properties disclosed herein. In aspects of this embodiment, a hydrogel composition comprising a glycosaminoglycan polymer and the at least one agent disclosed herein is processed using a heat treatment of, e.g., about 100° C., about 105° C., about 110° C., about 115° C., about 120° C., about 125° C., or about 130° C. In other aspects of this embodiment, a hydrogel composition comprising a glycosaminoglycan polymer and the at least one agent disclosed herein is processed using a heat treatment of, e.g., at least 100° C., at least 105° C., at least 110° C., at least 115° C., at least 120° C., at least 125° C., or at least 130° C. In yet other aspects of this embodiment, a hydrogel composition comprising a glycosaminoglycan polymer and the at least one agent disclosed herein is processed using a heat treatment of, e.g., about 100° C. to about 120° C., about 100° C. to about 125° C., about 100° C. to about 130° C., about 100° C. to about 135° C., about 110° C. to about 120° C., about 110° C. to about 125° C., about 110° C. to about 130° C., about 110° C. to about 135° C., about 120° C. to about 125° C., about 120° C. to about 130° C., about 120° C. to about 135° C., about 125° C. to about 130° C., or about 125° C. to about 135° C.

Long term stability of a hydrogel composition disclosed herein can be determined by subjecting a hydrogel composition to a heat treatment, such as, e.g., storage in an about 45° C. environment for about 60 days. Long term stability of a hydrogel composition disclosed herein can be evaluated 1) by assessing the clarity and color of a hydrogel composition after the 45° C. heat treatment, with a clear and uncolored hydrogel composition being indicative of a substantially stable hydrogel composition; 2) by determining the change in the extrusion force (EF) of a hydrogel composition disclosed herein after the 45° C. heat treatment, where the change in extrusion force less 2N is indicative of a substantially stable hydrogel composition as measured by (the extrusion force of a hydrogel composition with the specified additives before the 45° C. heat treatment) minus (the extrusion force of the a hydrogel composition with the specified additives after the 45° C. heat treatment); and/or 3) by determining the change in rheological properties of a hydrogel composition disclosed herein after sterilization, where the change in tan δ 1 Hz of less than 0.1 is indicative of a substantially stable hydrogel composition as measured by (tan δ 1 Hz of gel formulation with the specified additives before the 45° C. heat treatment) minus (tan δ 1 Hz of gel formulation with the specified additives after the 45° C. heat treatment). As such, a long term stability of a hydrogel composition disclosed herein is evaluated by retention of one or more of the following characteristics after the 45° C. heat treatment: clarity (transparency and translucency), homogeneousness, and cohesiveness.

In aspects of this embodiment, a hydrogel composition is substantially stable at room temperature for, e.g., about 3 months, about 6 months, about 9 months, about 12 months, about 15 months, about 18 months, about 21 months, about 24 months, about 27 months, about 30 months, about 33 months, or about 36 months. In other aspects of this embodiment, a hydrogel composition is substantially stable at room temperature for, e.g., at least 3 months, at least 6 months, at least 9 months, at least 12 months, at least 15 months, at least 18 months, at least 21 months, at least 24 months, at least 27 months, at least 30 months, at least 33 months, or at least 36 months. In other aspects of this embodiment, a hydrogel composition is substantially stable at room temperature for, e.g., about 3 months to about 12 months, about 3 months to about 18 months, about 3 months to about 24 months, about 3 months to about 30 months, about 3 months to about 36 months, about 6 months to about 12 months, about 6 months to about 18 months, about 6 months to about 24 months, about 6 months to about 30 months, about 6 months to about 36 months, about 9 months to about 12 months, about 9 months to about 18 months, about 9 months to about 24 months, about 9 months to about 30 months, about 9 months to about 36 months, about 12 months to about 18 months, about 12 months to about 24 months, about 12 months to about 30 months, about 12 months to about 36 months, about 18 months to about 24 months, about 18 months to about 30 months, or about 18 months to about 36 months.

The present compositions may optionally include, without limitation, other pharmaceutically acceptable components, including, without limitation, buffers, preservatives, tonicity adjusters, salts, antioxidants, osmolality adjusting agents, emulsifying agents, wetting agents, and the like.

A pharmaceutically acceptable buffer is a buffer that can be used to prepare a hydrogel composition disclosed herein, provided that the resulting preparation is pharmaceutically acceptable. Non-limiting examples of pharmaceutically acceptable buffers include acetate buffers, borate buffers, citrate buffers, neutral buffered salines, phosphate buffers, and phosphate buffered salines. Any concentration of a pharmaceutically acceptable buffer can be useful in formulating a pharmaceutical composition disclosed herein, with the proviso that a therapeutically effective amount of the active ingredient is recovered using this effective concentration of buffer. Non-limiting examples of concentrations of physiologically-acceptable buffers occur within the range of about 0.1 mM to about 900 mM. The pH of pharmaceutically acceptable buffers may be adjusted, provided that the resulting preparation is pharmaceutically acceptable. It is understood that acids or bases can be used to adjust the pH of a pharmaceutical composition as needed. Any buffered pH level can be useful in formulating a pharmaceutical composition, with the proviso that a therapeutically effective amount of the matrix polymer active ingredient is recovered using this effective pH level. Non-limiting examples of physiologically-acceptable pH occur within the range of about pH 5.0 to about pH 8.5. For example, the pH of a hydrogel composition disclosed herein can be about 5.0 to about 8.0, or about 6.5 to about 7.5, about 7.0 to about 7.4, or about 7.1 to about 7.3.

Pharmaceutically acceptable preservatives include, without limitation, sodium metabisulfite, sodium thiosulfate, acetylcysteine, butylated hydroxyanisole and butylated hydroxytoluene. Pharmaceutically acceptable preservatives include, without limitation, benzalkonium chloride, chlorobutanol, thimerosal, phenylmercuric acetate, phenylmercuric nitrate, a stabilized oxy chloro composition, such as, e.g., PURITE® (Allergan, Inc. Irvine, Calif.) and chelants, such as, e.g., DTPA or DTPA-bisamide, calcium DTPA, and CaNaDTPA-bisamide.

Pharmaceutically acceptable tonicity adjustors useful in a hydrogel composition disclosed herein include, without limitation, salts such as, e.g., sodium chloride and potassium chloride; and glycerin. The composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition disclosed herein. Other non-limiting examples of pharmacologically acceptable components can be found in, e.g., Ansel, supra, (1999); Gennaro, supra, (2000); Hardman, supra, (2001); and Rowe, supra, (2003), each of which is hereby incorporated by reference in its entirety.

Aspects of the present specification provide, in part, a method of treating a soft tissue condition of an individual by administering a hydrogel composition disclosed herein. As used herein, the term "treating," refers to reducing or eliminating in an individual a cosmetic or clinical symptom of a soft tissue condition characterized by a soft tissue imperfection, defect, disease, and/or disorder; or delaying or preventing in an individual the onset of a cosmetic or clinical symptom of a condition characterized by a soft tissue imperfection, defect, disease, and/or disorder. For example, the term "treating" can mean reducing a symptom of a condition characterized by a soft tissue defect, disease, and/or disorder by, e.g., at least 20%, at least 30%, at least 40%, at least 50%, at least 60%, at least 70%, at least 80%, at least 90% or at least 100%. The effectiveness of a hydrogel composition disclosed herein in treating a condition characterized by a soft tissue defect, disease, and/or disorder can be determined by observing one or more cosmetic, clinical symptoms, and/or physiological indicators associated with the condition. An improvement in a soft tissue defect, disease, and/or disorder also can be indicated by a reduced need for a concurrent therapy. Those of skill in the art will know the appropriate symptoms or indicators associated with specific soft tissue defect, disease, and/or disorder and will know how to determine if an individual is a candidate for treatment with a compound or composition disclosed herein.

A hydrogel composition in accordance with the invention is administered to an individual. An individual is typically a human being of any age, gender or race. Typically, any individual who is a candidate for a conventional procedure to treat a soft tissue condition is a candidate for a method disclosed herein. Although a subject experiencing the signs of aging skin is an adult, subjects experiencing premature aging or other skin conditions suitable for treatment (for example, a scar) can also be treated with a hydrogel composition disclosed herein. In addition, the presently disclosed hydrogel compositions and methods may apply to individuals seeking a small/moderate enlargement, shape change or contour alteration of a body part or region, which may not be technically possible or aesthetically acceptable with existing soft tissue implant technology. Pre-operative evaluation typically includes routine history and physical examination in addition to thorough informed consent disclosing all relevant risks and benefits of the procedure.

The hydrogel composition and methods disclosed herein are useful in treating a soft tissue condition. A soft tissue condition includes, without limitation, a soft tissue imperfection, defect, disease, and/or disorder. Non-limiting examples of a soft tissue condition include breast imperfection, defect, disease and/or disorder, such as, e.g., a breast augmentation, a breast reconstruction, mastopexy, micromastia, thoracic hypoplasia, Poland's syndrome, defects due to implant complications like capsular contraction and/or rupture; a facial imperfection, defect, disease or disorder, such as, e.g., a facial augmentation, a facial reconstruction, a mesotherapy, Parry-Romberg syndrome, lupus erythematosus profundus, dermal divots, scars, sunken checks, thin lips, nasal imperfections or defects, retro-orbital imperfections or defects, a facial fold, line and/or wrinkle like a glabellar line, a nasolabial line, a perioral line, and/or a marionette line, and/or other contour deformities or imperfections of the face; a neck imperfection, defect, disease or disorder; a skin imperfection, defect, disease and/or disorder; other soft tissue imperfections, defects, diseases and/or disorders, such as, e.g., an augmentation or a reconstruction of the upper arm, lower arm, hand, shoulder, back, torso including abdomen, buttocks, upper leg, lower leg including calves, foot including plantar fat pad, eye, genitals, or other body part, region or area, or a disease or disorder affecting these body parts, regions or areas; urinary incontinence, fecal incontinence, other forms of incontinence; and gastroesophageal reflux disease (GERD). As used herein, the term "mesotherapy" refers to a non-surgical cosmetic treatment technique of the skin involving intra-epidermal, intradermal, and/or subcutaneous injection of an agent administered as small multiple droplets into the epidermis, dermoepidermal junction, and/or the dermis.

The amount of a hydrogel composition used with any of the methods as disclosed herein will typically be determined based on the alteration and/or improvement desired, the reduction and/or elimination of a soft tissue condition symptom desired, the clinical and/or cosmetic effect desired by the individual and/or physician, and the body part or region being treated. The effectiveness of composition administration may be manifested by one or more of the following clinical and/or cosmetic measures: altered and/or improved soft tissue shape, altered and/or improved soft tissue size, altered and/or improved soft tissue contour, altered and/or improved tissue function, tissue ingrowth support and/or new collagen deposition, sustained engraftment of composition, improved patient satisfaction and/or quality of life, and decreased use of implantable foreign material.

Effectiveness of the compositions and methods in treating a facial soft tissue may be manifested by one or more of the following clinical and/or cosmetic measures: increased size, shape, and/or contour of facial feature like increased size, shape, and/or contour of lip, cheek or eye region; altered size, shape, and/or contour of facial feature like altered size, shape, and/or contour of lip, cheek or eye region shape; reduction or elimination of a wrinkle, fold or line in the skin; resistance to a wrinkle, fold or line in the skin; rehydration of the skin; increased elasticity to the skin; reduction or elimination of skin roughness; increased and/or improved skin tautness; reduction or elimination of stretch lines or marks; increased and/or improved skin tone, shine, brightness and/or radiance; increased and/or improved skin color, reduction or elimination of skin paleness; sustained engraftment of composition; decreased side effects; improved patient satisfaction and/or quality of life.

As yet another example, for urinary incontinence procedures, effectiveness of the compositions and methods for sphincter support may be manifested by one or more of the following clinical measures: decreased frequency of incontinence, sustained engraftment, improved patient satisfaction and/or quality of life, and decreased use of implantable foreign filler.

In aspects of this embodiment, the amount of a hydrogel composition administered is, e.g., about 0.01 g, about 0.05 g, about 0.1 g, about 0.5 g, about 1 g, about 5 g, about 10 g, about 20 g, about 30 g, about 40 g, about 50 g, about 60 g, about 70 g, about 80 g, about 90 g, about 100 g, about 150 g, or about 200 g. In other aspects of this embodiment, the amount of a hydrogel composition administered is, e.g., about 0.01 g to about 0.1 g, about 0.1 g to about 1 g, about 1 g to about 10 g, about 10 g to about 100 g, or about 50 g to about 200 g. In yet other aspects of this embodiment, the amount of a hydrogel composition administered is, e.g., about 0.01 mL, about 0.05 mL, about 0.1 mL, about 0.5 mL, about 1 mL, about 5 mL, about 10 mL, about 20 mL, about 30 mL, about 40 mL, about 50 mL, about 60 mL, about 70 g, about 80 mL, about 90 mL, about 100 mL, about 150 mL, or about 200 mL. In other aspects of this embodiment, the amount of a hydrogel composition administered is, e.g., about 0.01 mL to about 0.1 mL, about 0.1 mL to about 1 mL, about 1 mL to about 10 mL, about 10 mL to about 100 mL, or about 50 mL to about 200 mL.

The duration of treatment will typically be determined based on the cosmetic and/or clinical effect desired by the individual and/or physician and the body part or region being treated. In aspects of this embodiment, administration of a hydrogel composition disclosed herein can treat a soft tissue condition for, e.g., about 6 months, about 7 months, about 8 months, about 9 months, about 10 months, about 11 months, about 12 months, about 13 months, about 14 months, about 15 months, about 18 months, or about 24 months. In other aspects of this embodiment, administration of a hydrogel composition disclosed herein can treat a soft tissue condition for, e.g., at least 6 months, at least 7 months, at least 8 months, at least 9 months, at least 10 months, at least 11 months, at least 12 months, at least 13 months, at least 14 months, at least 15 months, at least 18 months, or at least 24 months. In yet aspects of this embodiment, administration of a hydrogel composition disclosed herein can treat a soft tissue condition for, e.g., about 6 months to about 12 months, about 6 months to about 15 months, about 6 months to about 18 months, about 6 months to about 21 months, about 6 months to about 24 months, about 9 months to about 12 months, about 9 months to about 15 months, about 9 months to about 18 months, about 9 months to about 21 months, about 6 months to about 24 months, about 12 months to about 15 months, about 12 months to about 18 months, about 12 months to about 21 months, about 12 months to about 24 months, about 15 months to about 18 months, about 15 months to about 21 months, about 15 months to about 24 months, about 18 months to about 21 months, about 18 months to about 24 months, or about 21 months to about 24 months.

Aspects of the present specification provide, in part, administering a hydrogel composition disclosed herein. As used herein, the term "administering" means any delivery mechanism that provides a composition disclosed herein to an individual that potentially results in a clinically, therapeutically, or experimentally beneficial result. The actual delivery mechanism used to administer a composition to an individual can be determined by a person of ordinary skill in the art by taking into account factors, including, without limitation, the type of skin condition, the location of the skin condition, the cause of the skin condition, the severity of the skin condition, the degree of relief desired, the duration of relief desired, the particular composition used, the rate of excretion of the particular composition used, the pharmacodynamics of the particular composition used, the nature of the other compounds included in the particular composition used, the particular route of administration, the particular characteristics, history and risk factors of the individual, such as, e.g., age, weight, general health and the like, or any combination thereof. In an aspect of this embodiment, a composition disclosed herein is administered to a skin region of an individual by injection.

The route of administration of a hydrogel composition to an individual patient will typically be determined based on the cosmetic and/or clinical effect desired by the individual and/or physician and the body part or region being treated. A composition disclosed herein may be administered by any means known to persons of ordinary skill in the art including, without limitation, syringe with needle, a pistol (for example, a hydropneumatic-compression pistol), catheter, topically, or by direct surgical implantation. The hydrogel composition disclosed herein can be administered into a skin region such as, e.g., a dermal region or a hypodermal region. For example, a hydrogel composition disclosed herein can be injected utilizing needles with a diameter of about 0.26 mm to about 0.4 mm and a length ranging from about 4 mm to about 14 mm. Alternately, the needles can be 21 to 32 G and have a length of about 4 mm to about 70 mm. Preferably, the needle is a single-use needle. The needle can be combined with a syringe, catheter, and/or a pistol.

In addition, a composition disclosed herein can be administered once, or over a plurality of times. Ultimately, the timing used will follow quality care standards. For example, a hydrogel composition disclosed herein can be administered once or over several sessions with the sessions spaced apart by a few days, or weeks. For instance, an individual can be administered a hydrogel composition disclosed herein every 1, 2, 3, 4, 5, 6, or 7 days or every 1, 2, 3, or 4 weeks. The administration a hydrogel composition disclosed herein to an individual can be on a monthly or bi-monthly basis or administered every 3, 6, 9, or 12 months.

Aspects of the present specification provide, in part, a dermal region. As used herein, the term "dermal region" refers to the region of skin comprising the epidermal-dermal junction and the dermis including the superficial dermis (papillary region) and the deep dermis (reticular region). The skin is composed of three primary layers: the epidermis, which provides waterproofing and serves as a barrier to infection; the dermis, which serves as a location for the appendages of skin; and the hypodermis (subcutaneous adipose layer). The epidermis contains no blood vessels, and is nourished by diffusion from the dermis. The main type of cells which make up the epidermis are keratinocytes, melanocytes, Langerhans cells and Merkels cells.

The dermis is the layer of skin beneath the epidermis that consists of connective tissue and cushions the body from stress and strain. The dermis is tightly connected to the epidermis by a basement membrane. It also harbors many Mechanoreceptor/nerve endings that provide the sense of touch and heat. It contains the hair follicles, sweat glands, sebaceous glands, apocrine glands, lymphatic vessels and blood vessels. The blood vessels in the dermis provide nourishment and waste removal from its own cells as well as from the Stratum basale of the epidermis. The dermis is structurally divided into two areas: a superficial area adjacent to the epidermis, called the papillary region, and a deep thicker area known as the reticular region.

The papillary region is composed of loose areolar connective tissue. It is named for its fingerlike projections called papillae that extend toward the epidermis. The papillae provide the dermis with a "bumpy" surface that interdigitates with the epidermis, strengthening the connection between the two layers of skin. The reticular region lies deep in the papillary region and is usually much thicker. It is composed of dense irregular connective tissue, and receives its name from the dense concentration of collagenous, elastic, and reticular fibers that weave throughout it. These protein fibers give the dermis its properties of strength, extensibility, and elasticity. Also located within the reticular region are the roots of the hair, sebaceous glands, sweat glands, receptors, nails, and blood vessels. Tattoo ink is held in the dermis. Stretch marks from pregnancy are also located in the dermis.

The hypodermis lies below the dermis. Its purpose is to attach the dermal region of the skin to underlying bone and muscle as well as supplying it with blood vessels and nerves. It consists of loose connective tissue and elastin. The main cell types are fibroblasts, macrophages and adipocytes (the hypodermis contains 50% of body fat). Fat serves as padding and insulation for the body.

In an aspect of this embodiment, a hydrogel composition disclosed herein is administered to a skin region of an individual by injection into a dermal region or a hypodermal region. In aspects of this embodiment, a hydrogel composition disclosed herein is administered to a dermal region of an individual by injection into, e.g., an epidermal-dermal junction region, a papillary region, a reticular region, or any combination thereof.

Advantageously, some of the present compositions are especially useful and effective in reducing appearance of fine lines, for example, in thin skin regions, of a patient. The skin region treated may be any skin region having fine lines or wrinkling, for example, due to age or UV exposure, and can be especially useful for treating, for example, and smoothing the appearance of, the tear trough region, forehead region, glabellar lines, or periorbital region.

For example, methods are provided for fine line treatment comprising the steps of administering to a dermal region of a patient a dermal filler composition as described elsewhere herein, at a depth of no greater than about 1 mm. When so administered, the compositions of these embodiments exhibit reduced or no perceptible blue discoloration when administered at a depth of no greater than about 1.0 mm, no greater than about 0.8 mm, no greater than about 0.6 mm, or no greater than about 4 mm or less into the dermal region.

Other aspects of the present specification disclose, in part, a method of treating a skin condition comprises the step of administering to an individual suffering from a skin condition a hydrogel composition disclosed herein, wherein the administration of the composition improves the skin condition, thereby treating the skin condition. In an aspect of this embodiment, a skin condition is a method of treating skin dehydration comprises the step of administering to an individual suffering from skin dehydration a hydrogel composition disclosed herein, wherein the administration of the composition rehydrates the skin, thereby treating skin dehydration. In another aspect of this embodiment, a method of treating a lack of skin elasticity comprises the step of administering to an individual suffering from a lack of skin elasticity a hydrogel composition disclosed herein, wherein the administration of the composition increases the elasticity of the skin, thereby treating a lack of skin elasticity. In yet another aspect of this embodiment, a method of treating skin roughness comprises the step of administering to an individual suffering from skin roughness a hydrogel composition disclosed herein, wherein the administration of the composition decreases skin roughness, thereby treating skin roughness. In still another aspect of this embodiment, a method of treating a lack of skin tautness comprises the step of administering to an individual suffering from a lack of skin tautness a hydrogel composition disclosed herein, wherein the administration of the composition makes the skin tauter, thereby treating a lack of skin tautness.

In a further aspect of this embodiment, a method of treating a skin stretch line or mark comprises the step of administering to an individual suffering from a skin stretch line or mark a hydrogel composition disclosed herein, wherein the administration of the composition reduces or eliminates the skin stretch line or mark, thereby treating a skin stretch line or mark. In another aspect of this embodiment, a method of treating skin paleness comprises the step of administering to an individual suffering from skin paleness a hydrogel composition disclosed herein, wherein the administration of the composition increases skin tone or radiance, thereby treating skin paleness. In another aspect of this embodiment, a method of treating skin wrinkles comprises the step of administering to an individual suffering from skin wrinkles a hydrogel composition disclosed herein, wherein the administration of the composition reduces or eliminates skin wrinkles, thereby treating skin wrinkles. In yet another aspect of this embodiment, a method of treating skin wrinkles comprises the step of administering to an individual a hydrogel composition disclosed herein, wherein the administration of the composition makes the skin resistant to skin wrinkles, thereby treating skin wrinkles.

In one aspect of the invention, dermal fillers are provided which are especially effective in treating and eliminating the appearance of fine lines, for example, relatively superficial, creases in the skin, for example, but not limited to, fine lines near the eyes, the tear trough region, forehead, periobital, glabellar lines, etc.

The appearance of a blue discoloration at the skin site where a dermal filler had been injected, (Tyndall effect) is a significant adverse event experienced by some dermal filler patients. Tyndall effect is more common in patients treated for superficial fine line wrinkles. Embodiments of the present invention have been developed which provide long lasting, translucent fillers which can be injected superficially to treat fine lines and wrinkles, even in regions of relatively thin skin, without any resulting blue discoloration from Tyndall effect. Fine lines or superficial wrinkles are generally understood to be those wrinkles or creases in skin that are typically found in regions of the face (forehead, lateral canthus, vermillion border/perioral lines) where the skin is thinnest, that is, the skin has a dermis thickness of less than 1 mm. On the forehead the average dermal thickness is about 0.95 mm for normal skin and about 0.81 mm for wrinkled skin. Dermis around the lateral canthus is even thinner (e.g. about 0.61 mm for normal skin and about 0.41 mm for wrinkled skin). The average outer diameter of a 30 or 32 gauge needle (needles that are typically used for fine line gel application) is about 0.30 and about 0.24 mm.

The present invention provides a dermal filler composition such as described elsewhere herein, which does not result in Tyndall effect, or does not result in any visually perceptible blue discoloration resulting from Tyndall effect.

Methods of treating fine lines in the skin of a patient are also provided. The methods generally comprise the steps of introducing into skin of a patient, a composition such as described herein. For example the compositions comprise a mixture of a hyaluronic acid component, a crosslinking component crosslinking the hyaluronic acid, and an additive other than the crosslinking component, the composition being substantially optically transparent; and wherein the dermal filler composition exhibits reduced Tyndall effect relative to composition that is substantially identical except without the additive.

In specific embodiments of the invention, gels are provided which are crosslinked with HMDA and have a G' of up to about 70 Pa, a G"/G' above about 0.65, an extrusion force of about 24 N or less, and a final HA concentration of up to about 25 mg/ml.

In other embodiments, gels are provided which are crosslinked with 4 AA, and have a G' of up to about 60 Pa, G"/G' above about 0.70, an extrusion force of about 30 N or less, and a final HA concentration of up to about 24 mg/ml.

In yet other embodiments, gels are provided which are crosslinked with lysine methyl ester, and have a G' of up to about 70 Pa, G"/G' above about 0.65, an extrusion force of about 24 N or less, and a final HA concentration of up to about 25 mg/ml.

Many of the dermal filler gels in accordance with the invention contain lidocaine, for example, at a lidocaine concentration of about 0.3 wt %.

These gels can be made as described herein, and are only provided as specific examples of compositions in accordance with the invention. Further examples are provided below.

EXAMPLES

Crosslinked HA Gels Via 1-ethyl-3-[3-dimethylaminopropyl]carbodiimide hydrochloride (EDC) Chemistry Preparation of crosslinked HA-based gels, in accordance with certain embodiments of the invention are described in Examples 1 and 2 below. In Example 1, the gel is made via EDC chemistry using crosslinker hexamethylene diamine (HMDA), and in Example 2, 3-[3-(3-amino propoxy)-2,2-bis(3-amino-propoxymethyl)-propoxy]-propylamine (4 arm amine-4 AA). Crosslinking is carried out under mild conditions, e.g. room temperature, for example, about 20 degrees C. to about 25 degrees C., and for example, at a low pH, for example, pH 5.4. The reactions conditions are tuned to prepare highly reticulate gels with optimal gel properties, excellent injectability and high final HA concentrations (~24 mg/ml). It has been discovered by the inventors that it may be advantageous to crosslink HA at very low hydration or reaction concentrations, with a moderate amount of either HMDA or 4 AA, in conjunction with 1-ethyl-3-(3-dimethylaminopropyl) carbodiimide hydrochloride (EDC) and N-hydroxysuccinimide (NHS) or sulfonyl-NHS (sulfo-NHS), the coupling agents. The advantages may be that ester linkage between HA may be reduced.

In an embodiment of the invention, a dermal filler composition for treatment of wrinkles in skin is provided wherein the composition comprises a hyaluronic acid component crosslinked with 3-[3-(3-amino propoxy)-2,2-bis(3-amino-propoxymethyl)-propoxy]-propylamine (4 AA) and a carbodiimide coupling agent.

Example 1

Formulation of HA-4 AA Hydrogel 13.33 g of 100 mM MES buffer pH 5.2 was added to a syringe containing 400.2 mg of low molecular weight (LMW) HA. The LMW HA may have a mean molecular weight of between about 310 KDa and about 840 KDa, for example, less than about 600 KDa.

4 AA solution was prepared by dissolving 492.1 mg 4 AA in 999.2 mg of 100 mM MES buffer pH 5.2, and adding 757 µl of 6 M HCl to bring the pH to 5.2.

EDC solution was prepared by dissolving 509.2 mg of EDC in 1156.4 mg 100 mM MES buffer pH 5.2, and in a separate vial, 175 mg of NHS was dissolved in 2635.8 mg of 100 mM MES buffer pH 5.2. Upon full hydration of the HA, for about 1 hour, 99 µl of the 4 AA solution was added to the hydrated HA. The mixture was homogenized by 10 times syringe-to-syringe mixing.

115 µl EDC solution, 115 µl NHS solution, and 140 µl of 100 mM MES buffer pH 5.2 were then added to the homogenized paste and mixed 10 times by syringe-to-syringe mixing.

The mixture was then transferred to a vial and crosslinked at room temperature for 5 hours, before the addition of 1.55 ml of 10×PBS buffer pH 7.4. The gel was allowed to swell for 3 days on a roller after which it was forced through a 60 µm pore-size mesh.

The sized gel was transferred to a cellulose ester membrane dialysis tubing MWCO 20 KDa and dialyzed against 1×PBS for 4 days, changing the buffer twice a day.

The gel was dispensed in 1 ml COO syringes, centrifuged at 5000 RPM for 5 min, and sterilized with moist steam. The gel had a final HA concentration of 26 mg/ml.

In another embodiment of the invention, a dermal filler composition for treatment of superficial wrinkles in skin is provided wherein the composition comprises a hyaluronic acid component crosslinked with a linear di-amine crosslinker, for example, hexamethylene diamine (HMDA) and a carbodiimide coupling agent. HMDA is the organic compound with the formula $H_2N(CH_2)_6NH_2$. The molecule is a diamine, consisting of a hexamethylene hydrocarbon chain terminated with amine functional groups. The dermal filler composition is administered into a dermal region of a patient to improve the appearance of skin.

Example 2

Formulation of a HA/HMDA Gel 20.0 g of 100 mM MES buffer pH 5.2 was added to a syringe containing 1000.7 mg of LMW HA.

HMDA solution was prepared by dissolving 522 mg HMDA.HCl in 2008.5 mg of 100 mM MES buffer pH 5.2, and adding 10 µl of 1 M NaOH to bring pH to 5.2.

EDC solution was prepared by dissolving 508 mg of EDC in 1188.5 mg 100 mM MES buffer pH 5.2, and in a separate vial, 44.2 mg of NHS was dissolved in 1340.7 mg of 100 mM MES buffer pH 5.2. Upon full hydration of the HA, for about 1 hour, 790 µl of the HMDA solution was added to the hydrated HA. The mixture was homogenized by 10 times syringe-to-syringe mixing.

490 µl EDC and 490 µl NHS solutions were then added to the homogenized paste. The mixture was again mixed 10 times by syringe-to-syringe mixing, and then transferred to a vial and crosslinked at room temperature for 5 hours, before the addition of 18.0 ml of 1×PBS buffer pH 7.4.

The gel was allowed to swell for 3 days on a roller before it was force through a 60 µm pore size mesh. The sized gel was placed in a cellulose ester membrane dialysis tubing MWCO 20 KDa and dialyzed against 70% IPA for 30 min, before the dialysis medium was changed to 1×PBS. The gel was then dialyzed for 4 days changing the buffer twice a day.

The gel was dispensed in 1 ml COC syringes, centrifuged at 5000 RPM for 5 min to remove air bubbles, and sterilized with moist steam. The final HA concentration of the gel was 25 mg/ml.

In yet another embodiment of the invention, a dermal filler composition for treatment of superficial wrinkles in skin is provided wherein the composition comprises a hyaluronic acid component crosslinked with lysine methyl ester and a carbodiimide coupling agent. Lysine is an essential amino acid and has chemical formula $C_6H_{14}N_2O_2$.

Example 3

Formulation of a HA/Lysine Hydrogel 400.5 mg of LMW HA was hydrated for 30 min. in a syringe by adding 8.0 g of 100 mM MES buffer pH 5.2. Lysine methyl ester (LME) solution was prepared by dissolving 400.3 mg of LME.HCl in 1046.6 mg of 100 mM MES buffer pH 5.2 in a vial. EDC solution was prepared by dissolving 288 mg of EDC in 1357.1 mg of 100 mM MES buffer pH 5.2 in a small vial, and NHS solution was prepared by dissolving 61.0 mg of NHS in 962.8 mg of 100 mM MES buffer pH 5.2 in a separate vial. Upon complete hydration of HA, 261 µl of LME solution was added to the hydrated HA. The mixture was homogenized by syringe-to-syringe mixing, 10 times, before adding 387 µl of EDC solution and 372 µl of NHS solution. The paste was again mixed 10 times by syringe-to-syringe mixing. The mixture was then transferred to a vial and crosslinked at room temperature for 5 h. 6.21 ml of 1×PBS buffer pH 7.4 was then added to the crosslinked gel. The gel was allowed to swell for 3 days on a roller before it was sized by forcing it through a 60 µm pore size stainless steel mesh. To convert this HA-lysine methyl ester hydrogel to HA-lysine hydrogel, a small amount of NaOH solution was added to the gel and mix to raise the gel pH to about 12. The mixture was then placed in a water bath set at 50° C. for 5 min before the addition of hydrochloric acid to bring back the pH to ~7.4. The gel was then placed in a cellulose ester membrane dialysis tubing MWCO 20 KDa and dialyzed against 70% IPA for 30 min, before the dialysis medium was changed to 1×PBS. The gel was dispensed in 1 ml COO syringes, centrifuged at 5000 RPM for 5 min to remove air bubbles, and sterilized with moist steam. The final HA concentration of the gel was 26 mg/ml.

Example 4

Determination of Rheological Properties of Gels of Examples 1-3

An Oscillatory parallel plate rheometer, Anton Paar Physica MCR 301, was used to measure the rheological properties of the gels. A plate diameter of 25 mm was used at a gap height of 1 mm. Measurements were done at a constant temperature of 25° C. Each measurement consisted of a frequency sweep from 1 to 10 Hz at a constant strain of 2% and a logarithmic increase of frequency followed by a strain sweep from 1 to 300% at a constant frequency of 5 Hz with a logarithmic increase in strain. The storage modulus (G') and the viscous modulus (G") were obtained from the strain sweep at 1% strain.

TABLE 2

Storage and viscous moduli of gels obtained from Example 1 to Example 3

| Sample ID | Storage Modulus (G') Pa | Viscous Modulus (G") Pa |
|---|---|---|
| Example 1 | 263 | 49 |
| Example 2 | 340 | 43 |
| Example 3 | 560 | 90 |

Example 5

Extrusion Force Measurements of Gels of Examples 1-3

The force required to extrude the gels through a 30 gauge needle was measured using an Instron 5564 and a Bluehill 2 software. The gels were extruded from a 1 ml COO syringe through a 30 G½ TSK needle. The plunger was pushed at a speed of 100 mm/min for 11.35 mm, and the extrusion force was recorded.

TABLE 3

Extrusion force of gels obtained from Example 1 to Example 3

| Sample ID | Extrusion force (N) |
|---|---|
| Example 1 | 89 |
| Example 2 | 32 |
| Example 3 | 30 |

Example 6

Biocompatibility Testing of Gels of Examples 1-3

50 µl bolus injections of gel were implanted intradermally in the dorsal surface of Sprague Dawley rats. The implants were removed at 1 week and analyzed by histology with hematoxylin and eosin (H&E) staining, and CD68 staining which is a marker for mononuclear inflammation cells. Three 20× images of CD68 were scored from 0-4 based on the degree of staining. These values were then averaged out to give a sample score. Four samples were analyzed from each gel. Materials with score above 3.1 are believed to be pro-inflammatory.

TABLE 4

Average CD68 scores of hydrogels from Examples 1 to 3

| Sample ID | Average CD68 score |
| --- | --- |
| Example 1 | 1.4 |
| Example 2 | 2.4 |
| Example 3 | 2.1 |

Example 7

Cytotoxicity Testing of Gels of Examples 1-3

In Vitro cytotoxicity tests of the gels were performed by NAMSA according to the Agarose Overlay Method of ISO 10993-5: biological Evaluation of Medical Devices—Part 5: Tests for In Vitro Cytotoxicity. Triplicate wells were dosed with 0.1 ml of test articles placed on a filtered disc, as well as 0.9% NaCl solution, 1 cm length of high density polyethylene as a negative control, and 1×1 $cm^2$ portion of latex as a positive control. Each was placed on an agarose surface directly overlaying a monolayer of L929 mouse fibroblast cells. After incubating at 37° C. in 5% $CO_2$ for 24 h. The cultures were examined macroscopically and microscopically for any abnormal cell morphology and cell lysis. The test articles were scored from 0-4 based on the zone of lysis in the proximity of the samples. Test materials from Examples 1, 2, and 3 scored 0 as test articles showed no evidence of causing any cell lysis or toxicity.

Example 8

Crosslinking HA with 4 AA Using EDC and NHS as Coupling Agents 32.55 g of 100 mM MES buffer pH 5.2 was added to a syringe containing 1000.4 mg of LMW HA. 4 AA solution was prepared by dissolving 256.3 mg 4 AA in 1039.8 mg of 100 mM MES buffer pH 5.2, and adding 380 µl of 6 M HCl to bring pH to 5.2. EDC solution was prepared by dissolving 251.2 mg of EDC in 1013.8 mg 100 mM MES buffer pH 5.2, and in a separate vial, 74.7 mg of NHS was dissolved in 2020.0 mg of 100 mM MES buffer pH 5.2. Upon full hydration of the HA, ~1 h, 260 µl of the 4 AA solution was added to the hydrated HA. The mixture was homogenized by 10 times syringe-to-syringe mixing. 277 µl EDC and 273 µl NHS solutions were then added to the homogenized paste and again mix 10 times by syringe-to-syringe mixing. The mixture was then transferred to a vial and crosslinked at room temperature for 5 h. before the addition of 6.4 ml of 10×PBS buffer pH 7.4. The gel was allowed to swell for 3 days on a roller before it was force through a 60 µm pore size mesh. The sized gel was placed in a cellulose ester membrane dialysis tubing MWCO 20 KDa and dialyzed against 1×PBS for 4 days changing the buffer twice a day. The gel was dispensed in 1 ml COC syringes, centrifuge at 5000 RPM for 5 min, and sterilized with moist steam. The gel had a final HA concentration of 23 mg/ml.

Example 9

Crosslinking HA with HMDA Using EDC and NHS as Coupling Agents 20.0 g of 100 mM MES buffer pH 5.2 was added to a syringe containing 1000.0 mg of LMW HA. HMDA solution was prepared by dissolving 260.9 mg HMDA hydrochloride in 2010.5 mg of 100 mM MES buffer pH 5.2, and adding 2 µl of 1 M NaOH to bring pH to 5.2. EDC solution was prepared by dissolving 254.2 mg of EDC in 1188.4 mg 100 mM MES buffer pH 5.2, and in a separate vial, 44.3 mg of NHS was dissolved in 1341.8 mg of 100 mM MES buffer pH 5.2. Upon full hydration of the HA, 1 h, 790 µl of the HMDA solution was added to the hydrated HA. The mixture was homogenized by 10 times syringe-to-syringe mixing. 490 µl EDC and 490 µl NHS solutions were then added to the homogenized paste and again mixed 10 times by syringe-to-syringe mixing. The mixture was then transferred to a vial and crosslinked at room temperature for 5 h. before the addition of 17.9 ml of 1×PBS buffer pH 7.4. The gel was allowed to swell for 3 days on a roller before it was forced through a 60 µm pore size mesh. The sized gel was placed in a cellulose ester membrane dialysis tubing MWCO 20 KDa and dialyzed against 1×PBS for 4 days changing the buffer twice a day. The gel was dispensed in 1 ml COC syringes, centrifuge at 5000 RPM for 5 min, and sterilized with moist steam. The final HA concentration of the gel was 25 mg/ml.

Example 10

HA-Lysine Hydrogels Using EDC and NHS as Coupling Agents 8.06 g of 100 mM MES buffer pH 5.2 was added to a syringe containing 400.3 mg of LMW HA. Lysine methylester hydrochloride solution was prepared by dissolving 400.3 mg lysine methylester hydrochloride in 1046.6 mg of 100 mM MES buffer pH 5.2. EDC solution was prepared by dissolving 287.6 mg of EDC in 1364.6 mg 100 mM MES buffer pH 5.2, and in a separate vial, 60.2 mg of NHS was dissolved in 962.8 mg of 100 mM MES buffer pH 5.2. Upon full hydration of the HA, ~1 h, 132 µl of the lysine methylester hydrochloride solution was added to the hydrated HA. The mixture was homogenized by 10 times syringe-to-syringe mixing. 196 µl EDC and 190 µl NHS solutions were then added to the homogenized paste and again mixed 10 times by syringe-to-syringe mixing. The mixture was then transferred to a vial and crosslinked at room temperature for 5 h. before the addition of 6.67 ml of 1×PBS buffer pH 7.4. The gel was allowed to swell for 3 days on a roller before it was forced through a 60 µm pore size mesh. To convert HA-lysine methyl ester hydrogel to HA-lysine hydrogel, a small amount of NaOH solution was added to the gel and mix to raise the gel pH to about 12. The mixture was then placed in a water bath set at 50° C. for 5 min before the addition of hydrochloric acid to bring back the pH to ~7.4. The sized gel was placed in a cellulose ester membrane dialysis tubing MWCO 20 KDa and dialyzed against 1×PBS for 4 days changing the buffer twice a day. The gel was dispensed in 1 ml COC syringes, centrifuge at 5000 RPM for 5 min, and sterilized with moist steam. The gel had a final HA concentration of 26 mg/ml.

Example 11

Gels Containing Lidocaine 1858 mg of lidocaine HCl was added into a 5 ml volumetric flask. The flask was topped to the mark with 1×PBS buffer to give a lidocaine HCl concentration of 372 mg/ml. 200 µl of this lidocaine solution was then added to 24.5 mg of gel from Examples 8, 9 and 10 in a syringe. The mixture was forced to another syringe through a connector. This process was repeated 20 times to obtain a homogenous mixture.

Example 12

Determination of Rheological Properties of Gels in Examples 8-10

An Oscillatory parallel plate rheometer, Anton Paar Physica MCR 301, was used to measure the rheological properties of the gels. A plate diameter of 25 mm was used at a gap height of 1 mm. Measurements were done at a constant temperature of 25° C. Each measurement consisted of a frequency sweep from 1 to 10 Hz at a constant strain of 2% and a logarithmic increase of frequency followed by a strain sweep from 1 to 300% at a constant frequency of 5 Hz with a logarithmic increase in strain. The storage modulus (G') and the viscous modulus (G") were obtained from the strain sweep at 1% strain.

TABLE 5

Storage and viscous moduli of gels obtained from Example 8 to Example 10

| Sample ID | Storage Modulus (G') Pa | Viscous Modulus (G") Pa |
|---|---|---|
| Example 8 | 41 | 29.5 |
| Example 9 | 67 | 42 |
| Example 10 | 66 | 40 |

Example 13

Extrusion Force Measurements of Gels in Examples 8-10

The force required to extrude the gels through a 30 gauge needle was measured using an Instron 5564 and a Bluehill 2 software. The gels were extruded from a 1 ml COO syringe through a 30 G½ TSK needle. The plunger was pushed at a speed of 100 mm/min for 11.35 mm, and the extrusion force was recorded.

TABLE 6

Extrusion force of gels obtained from example 1 to example 4

| Sample ID | Extrusion force (N) |
|---|---|
| Example 8 | 19.5 |
| Example 9 | 22 |
| Example 10 | 22 |

Example 14

Cytotoxicity Testing of Gels, ISO 10993-5, Examples 8-10

In Vitro cytotoxicity tests of the gels were performed by NAMSA according to the Agarose Overlay Method of ISO 10993-5: biological Evaluation of Medical Devices—Part 5: Tests for In Vitro Cytotoxicity. Triplicate wells were dosed with 0.1 ml of test articles placed on a filtered disc, as well as 0.9% NaCl solution, 1 cm length of high density polyethylene as a negative control, and 1×1 $cm^2$ portion of latex as a positive control. Each was placed on an agarose surface directly overlaying a monolayer of L929 mouse fibroblast cells. After incubating at 37° C. in 5% $CO_2$ for 24 h. the cultures were examined macroscopically and microscopically for any abnormal cell morphology and cell lysis. The test articles were scored from 0-4 based on the zone of lysis in the proximity of the samples. Test materials from examples 8, 9 and 10 scored 0 as test articles showed no evidence of causing any cell lysis or toxicity.

Example 15

Tyndall Evaluation of Gels

In order to further support visual observations and carry out comparative performance analysis of HA fillers, quantitative analysis of Tyndall effect was performed. Based on existing scientific understanding on light scattering and interaction of light with skin, two distinct approaches based on (a) colorimetry, and (b) spectroscopy were employed to quantify Tyndall effect in skin. Based on these techniques three distinct quantitative parameters (outlined below) were defined to measure Tyndall effect in vivo.

Tyndall Effect Visual Score:

The scale had a range of 1 to 5 with increments of 0.5. A score of 1 was given to injection sites with normal skin tone and no blue discoloration. A maximum score of 5 was given to thick and pronounced blue discoloration (typically associated with Restylane or Juvéderm Ultra Plus). Three independent observers were trained on the scale before being blinded to score test samples.

Blue Component of Skin Color—"b":

A chromameter (CM2600D, Konica Minolta, NJ) was used to quantify the blue color component of light remitted from skin sites injected with the various fillers. This was achieved by using the "b" component of L-a-b color scale.

"% Blue Light" Remitted from Skin:

A portable spectrophotometer (CM2600D, Konica Minolta, NJ) was used to quantify the % blue light remitted from skin in the total visible light range. This was achieved by integrating the area under the visible light spectrum between 400-490 nm and normalizing it by the total area under the spectrum (400-700 nm).

Gels of the present disclosure and commercial gels were injected intradermally through a 27 G½ TSK needle using linear threading technique into the thighs of two months old hairless rats. The gels were implanted superficially to mimic clinical fine line procedures. Tests for Tyndall are performed 48 h after gel implantation. Before performing the Tyndall tests, the animals are euthanized to improve contrast of the Tyndall effect.

2 days after implantation of the gels it was found that gels of Examples 8 to 10 exhibited no discernible Tyndall effect. Commercial fine line gels (Juvederm Refine and Restylane Touch, showed a marked bluish discoloration. (See FIG. 1).

A visual score of 1-5 with increments of 0.5, was used to score the injection sites. Injection sites with score of 1 showed no skin discoloration, while injections sites with score of 5 showed severe blue discoloration of the skin. Spectroscopic analysis were also performed on the injection sites with the aid of a chromatometer (CM2600D, Konica Minolta, NJ). The blue component of skin color "b", and the % of blue light remitted from skin (400-700 nm) were independently measured. Gels of Examples 8-10 exhibited no discernible Tyndall effect, and had lower visual Tyndall score and % of blue light remitted values. The Tyndall score and % of remitted blue light values were higher for the commercial gels.

Example 16

In Vivo Duration Evaluation of Gels, by MRI

150 μl of gel compositions of Examples 8 and 9, in accordance with the invention, were injected intradermally on six different location on the dorsal side of female Sprague-Dawley rats; two contralateral sites caudal to shoulder blades, two medial sites directly between caudal and rostral sites, and two contralateral sites slightly rostral from knee, each location containing a different formulation. MRI scanning was performed with a 7 Tesla 70/30 Bruker Biospec instrument. Scanning was performed immediately after gel implantation (baseline), 12 weeks after gel implantation, and 24 weeks after gel implantation. In vivo degradation and gel stability was determined by calculating the volume, surface area, and surface area to volume ratio at each time point.

As shown, the present gels show substantial improvement in longevity in vivo when compared to Commercial Fine Line Filler III (Belotero Soft), a commercial HA-based dermal filler that is marketed as being useful for treating superficial wrinkles in skin.

Example 17

Compositions of the Invention for Treatment of Periorbital Lines

A 40 year old thin woman presents with fine wrinkles in the periorbital region and requests dermal filler treatment. Using a 30 gauge needle, the physician introduces 0.6 ml of a HA-based gel in accordance with the invention (such as that described in Example 8) superficially into the fine lines beneath her eyes and in the tear trough region using linear threading technique. Although the gel is introduced superficially, no blue discoloration is observed and the patient is satisfied with the results.

Example 18

Compositions of the Invention for Treatment of Periorbital Lines

A 35 year old man having Fitzpatrick skin type III presents with fine wrinkles in the glabellar region and requests dermal filler treatment. Using a 27 gauge needle, the physician introduces 1.0 ml of a HA-based gel in accordance with the invention (such as that described in Example 9) superficially, about 0.8 mm deep, into the glabellar lines using conventional technique. Although the gel is introduced, no blue discoloration is observed. Two weeks after treatment, there is still no bluish discoloration. The patient reports he is satisfied with the results.

In closing, it is to be understood that although aspects of the present specification have been described with reference to the various embodiments, one skilled in the art will readily appreciate that the specific examples disclosed are only illustrative of the principles of the subject matter disclosed herein. Therefore, it should be understood that the disclosed subject matter is in no way limited to a particular methodology, protocol, and/or reagent, etc., described herein. As such, those skilled in the art could make numerous and various modifications or changes to or alternative configurations of the disclosed subject matter can be made in accordance with the teachings herein without departing from the spirit of the present specification. Changes in detail may be made without departing from the spirit of the invention as defined in the appended claims. Lastly, the terminology used herein is for the purpose of describing particular embodiments only, and is not intended to limit the scope of the present invention, which is defined solely by the claims. In addition, it is intended that all matter contained in the above description or shown in the accompanying drawings shall be interpreted as illustrative only and not limiting. Accordingly, the present invention is not limited to that precisely as shown and described.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing quantities of ingredients, properties such as molecular weight, reaction conditions, and so forth used in the specification and claims are to be understood as being modified in all instances by the term "about." As used herein, the term "about" means that the item, parameter or term so qualified encompasses a range of plus or minus ten percent above and below the value of the stated item, parameter or term. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

What is claimed is:

1. A method of treating wrinkles in skin of a patient, the method comprising administering a hydrogel dermal filler composition into a dermal region of the patient, wherein the composition comprises lysine-crosslinked hyaluronic acid gel particles having a size ranging from about 10 µm to about 1000 µm in diameter, wherein the lysine-crosslinked hyaluronic acid is present in the composition at a concentration of between about 10 mg/mL and about 40 mg/mL, wherein the lysine has a chemical formula of $C_6H_{14}N_2O_2$, and wherein the hydrogel composition comprises fluid comprising uncrosslinked hyaluronic acid with a mean molecular weight from 100 kDa to 300 kDa.

2. The method of claim 1, wherein the dermal region is a tear trough region, a glabellar line, a periorbital region or a forehead region.

3. The method of claim 1, wherein the lysine-crosslinked hyaluronic acid is present in the composition at a concentration of between about 14 mg/mL and about 30 mg/mL.

4. The method of claim 1, wherein the lysine-crosslinked hyaluronic acid is present in the composition at a concentration of between about 18 mg/mL and about 30 mg/mL.

5. The method of claim 1, wherein the degree of crosslinking is between about 3% and about 12%.

6. The method of claim 1, wherein the degree of crosslinking is between about 5% and about 10%.

7. The method of claim 1, wherein the hydrogel dermal filler composition has a storage modulus of up to about 70 Pa.

8. The method of claim 1, wherein the hydrogel dermal filler composition has a viscous modulus of 40 Pa or greater.

9. The method of claim 1, wherein the hydrogel dermal filler composition has an extrusion force of about 24N or less.

10. The method of claim 1, wherein the administration of the hydrogel dermal filler composition into the dermal region of the patient does not result in a Tyndall effect.

11. A method of administering a hydrogel composition, the method comprising:
administering the hydrogel composition into a dermal region of a patient,
wherein the hydrogel composition comprises lysine-crosslinked hyaluronic acid gel particles having a size ranging from about 10 µm to about 1000 µm in diameter, and wherein the lysine-crosslinked hyaluronic acid is present in the composition at a concentration of between about 10 mg/mL and about 40 mg/mL, and wherein the hydrogel composition comprises fluid comprising uncrosslinked hyaluronic acid with a mean molecular weight from 100 kDa to 300 kDa.

12. The method of claim 11, wherein the hydrogel composition is administered into the dermal region at a depth of no greater than 1 mm.

13. The method of claim 11, wherein the hydrogel composition is administered to add volume and fullness to the dermal region.

14. The method of claim 11, wherein the hydrogel composition is administered to reduce wrinkles and fine lines in the dermal region.

15. The method of claim 11, wherein the hydrogel composition is administered to treat a soft tissue condition.

16. The method of claim 11, wherein the administration of the hydrogel composition does not cause a perceptible blue discoloration.

17. The method of claim 11, wherein the hydrogel composition is administered by injection using a 32 gauge or smaller needle.

18. The method of claim 11, wherein the hydrogel composition is administered in an amount from about 0.01 mL to about 200 mL.

19. The method of claim 11, wherein the hydrogel composition is administered by injection into a hypodermal region.

20. The method of claim 11, wherein the hydrogel composition is administered by injection into an epidermal-dermal junction region, a papillary region, a reticular region, or any combination thereof.

21. The method of claim 11, wherein the lysine has a chemical formula of $C_6H_{14}N_2O_2$.

22. The method of claim 1, wherein the hydrogel dermal filler composition is steam sterilized.

23. The method of claim 11, wherein the hydrogel composition is steam sterilized.

24. A method of treating wrinkles in skin of a patient, the method comprising
administering a hydrogel dermal filler composition comprising lysine-crosslinked hyaluronic acid gel particles into a dermal region of the patient,
wherein the lysine has a chemical formula of $C_6H_{14}N_2O_2$, and wherein the hydrogel composition comprises fluid comprising uncrosslinked hyaluronic acid with a mean molecular weight from 100 kDa to 300 kDa.

25. The method of claim 24, wherein the lysine-crosslinked hyaluronic acid gel particles have a size ranging from about 10 μm to about 1000 μm in diameter.

26. The method of claim 24, wherein the lysine-crosslinked hyaluronic acid is present in the composition at a concentration of between about 10 mg/mL and about 40 mg/mL.

* * * * *